(12) United States Patent
Morhet et al.

(10) Patent No.: US 8,759,075 B2
(45) Date of Patent: Jun. 24, 2014

(54) BIOLOGIC SAMPLE COLLECTION DEVICES AND METHODS OF PRODUCTION AND USE THEREOF

(75) Inventors: Jeff Morhet, Gilbert, AZ (US); Thomas J Kindt, Placitas, NM (US); Franco A Ferrari, La Jolla, CA (US); Frederic Zenhausern, Fountain Hills, AZ (US); Vasana Maneeratana, Phoenix, AZ (US); Deirdre Morhet, legal representative, Gilbert, AZ (US)

(73) Assignee: Diomics Corporation, La Jolla, CA (US)

( * ) Notice: Subject to any disclaimer, the term of this patent is extended or adjusted under 35 U.S.C. 154(b) by 0 days.

(21) Appl. No.: 13/548,643

(22) Filed: Jul. 13, 2012

(65) Prior Publication Data

US 2014/0017676 A1 Jan. 16, 2014

(51) Int. Cl.
*C12M 1/00* (2006.01)
*C12Q 1/68* (2006.01)
*C12M 1/34* (2006.01)
*C12M 3/00* (2006.01)

(52) U.S. Cl.
USPC .... 435/283.1; 435/6.1; 435/287.1; 435/287.2

(58) Field of Classification Search
CPC ....... A61K 39/21; A61K 39/39; A61K 9/006; C12N 2740/16111; C12N 2770/24211
See application file for complete search history.

(56) References Cited

U.S. PATENT DOCUMENTS

| | | | |
|---|---|---|---|
| 5,916,802 A * | 6/1999 | Andreotti | 435/287.7 |
| 6,268,222 B1 * | 7/2001 | Chandler et al. | 436/523 |
| 7,790,865 B1 | 9/2010 | Heath et al. | |
| 7,927,548 B2 | 4/2011 | Slowey et al. | |
| 7,978,074 B2 | 7/2011 | Nikitin et al. | |
| 8,049,623 B2 | 11/2011 | Morris et al. | |
| 2003/0129738 A1 * | 7/2003 | Sorenson et al. | 435/287.1 |
| 2007/0167900 A1 | 7/2007 | Kanjilal et al. | |
| 2010/0226960 A1 * | 9/2010 | Chudzik et al. | 424/426 |
| 2010/0274155 A1 * | 10/2010 | Battrell et al. | 600/572 |
| 2010/0317051 A1 | 12/2010 | Hanselle et al. | |
| 2011/0001609 A1 * | 1/2011 | Oldham et al. | 340/10.1 |

(Continued)

FOREIGN PATENT DOCUMENTS

EP 2249140 11/2010
WO 2006089297 8/2006

(Continued)

OTHER PUBLICATIONS

Zhang et al, Nanotechnology, vol. 20, pp. 1-14, published Jun. 16, 2009.*

(Continued)

*Primary Examiner* — Robert T. Crow
(74) *Attorney, Agent, or Firm* — Novak Druce Connolly Bove + Quigg LLP; Amy A. Dobbelaere

(57) ABSTRACT

Collection devices and kits for biological sample collection include a biologic sample collection device having a hydrophilic swab matrix that includes a modified polycaprolactone (PCL). Methods of production and use thereof are also described herein. The biologic sample collection devices, kits and methods described herein are used to collect a biologic sample (e.g., blood, buccal cells, etc.) and to enable extraction of nucleic acids (e.g., DNA) from that biologic sample so that the nucleic acids can be analyzed (e.g., sequencing and subsequent analysis of DNA).

43 Claims, 13 Drawing Sheets

(56) References Cited

U.S. PATENT DOCUMENTS

| | | | |
|---|---|---|---|
| 2011/0008771 A1 | 1/2011 | Hanselle et al. | |
| 2012/0034601 A1 | 2/2012 | Zenhausern et al. | |
| 2012/0149021 A1 | 6/2012 | Yung et al. | |

FOREIGN PATENT DOCUMENTS

| | | |
|---|---|---|
| WO | 2009012808 | 1/2009 |
| WO | 2010123462 | 10/2010 |
| WO | 2011094745 | 8/2011 |
| WO | 2012024407 | 2/2012 |

OTHER PUBLICATIONS

Armani, et al., "Microfabrication technology for polycaprolactone, a biodegradable polymer", J. Micromech. Microeng. vol. 10 (2000), pp. 80-84.

B. Alp, et al., "Crystallization Control of Polycaprolactone (PCL) with Inorganic and Organic Additives", 4 Pgs. Poster presented at the 18th International Symposium on Industrial Crystallization, Zurich, Switzerland, Sep. 16, 2011.

Naidoo, et al., "An emulsion preparation for novel micro-porous polymeric hemi-shells", Material Letters vol. 62, 2008, pp. 252-254.

Perego, et al., "Functionalization of poly-L-lactic-co-e-caprolactone: effects of surface modification on endothelial cell proliferation and hemocompatibility", Improved endothelial adhesion for small diameter graft, J. Biomater. Sci. Polymer Edn, vol. 14, No. 10, 2003, pp. 1057-1075.

Pok, et al., "In vitro characterization of polycaprolactone matrices generated in aqueous media", Acta Biomater, 6(3): 1061-1068. Mar. 2010.

Thapa, et al., "Polymers with nando-dimensional surface features enhance bladder smooth muscle cell adhesion", Enhancement of Bladder SMC Adhesion, Wiley Periodicals, Inc., 2003, pp. 1374-1383.

Woodruff, et al., "The return of a forgotten polymer-Polycaprolactone in the 21st Century", Progress in Polymer Science, vol. 35, Oct. 2010, pp. 1217-1256.

International Search Report and the Written Opinion of the ISA mailed on Dec. 20, 2013 in international Application No. PCT/US2013/049560. (17 pages).

Spiess et al., "Trehalose is a potent PCR enhancer: Lowering of DNA melting temperature and thermal stabilization of Taq Polymerase by the disaccharide trehalose", Clin Chem (Jul. 2004) 50(7): 1256-1259.

* cited by examiner

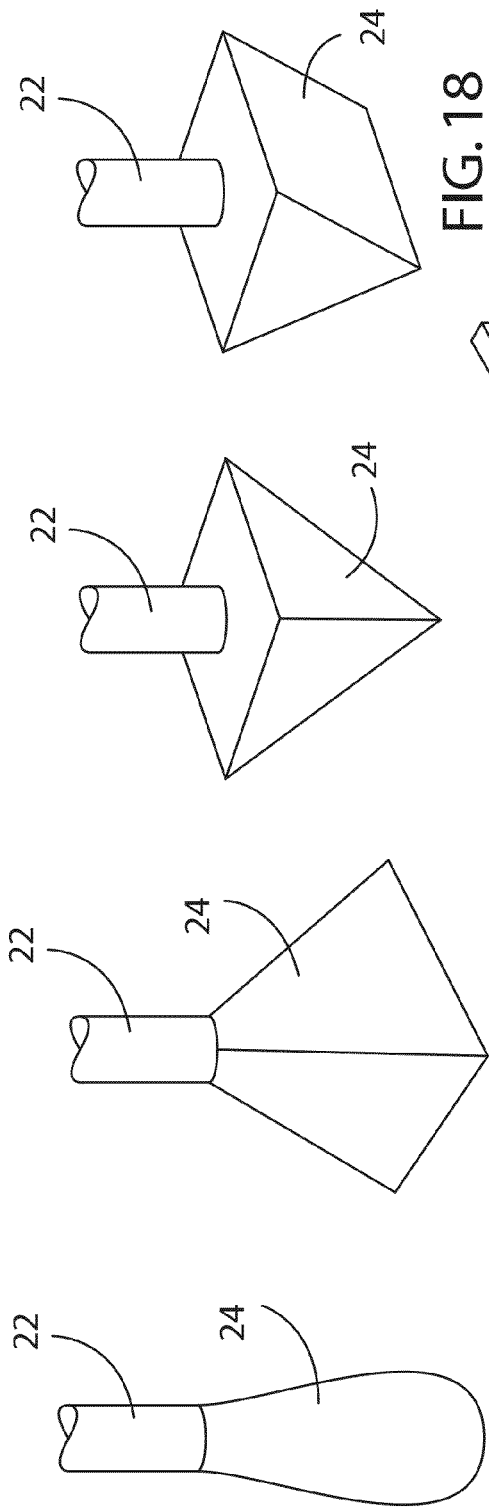

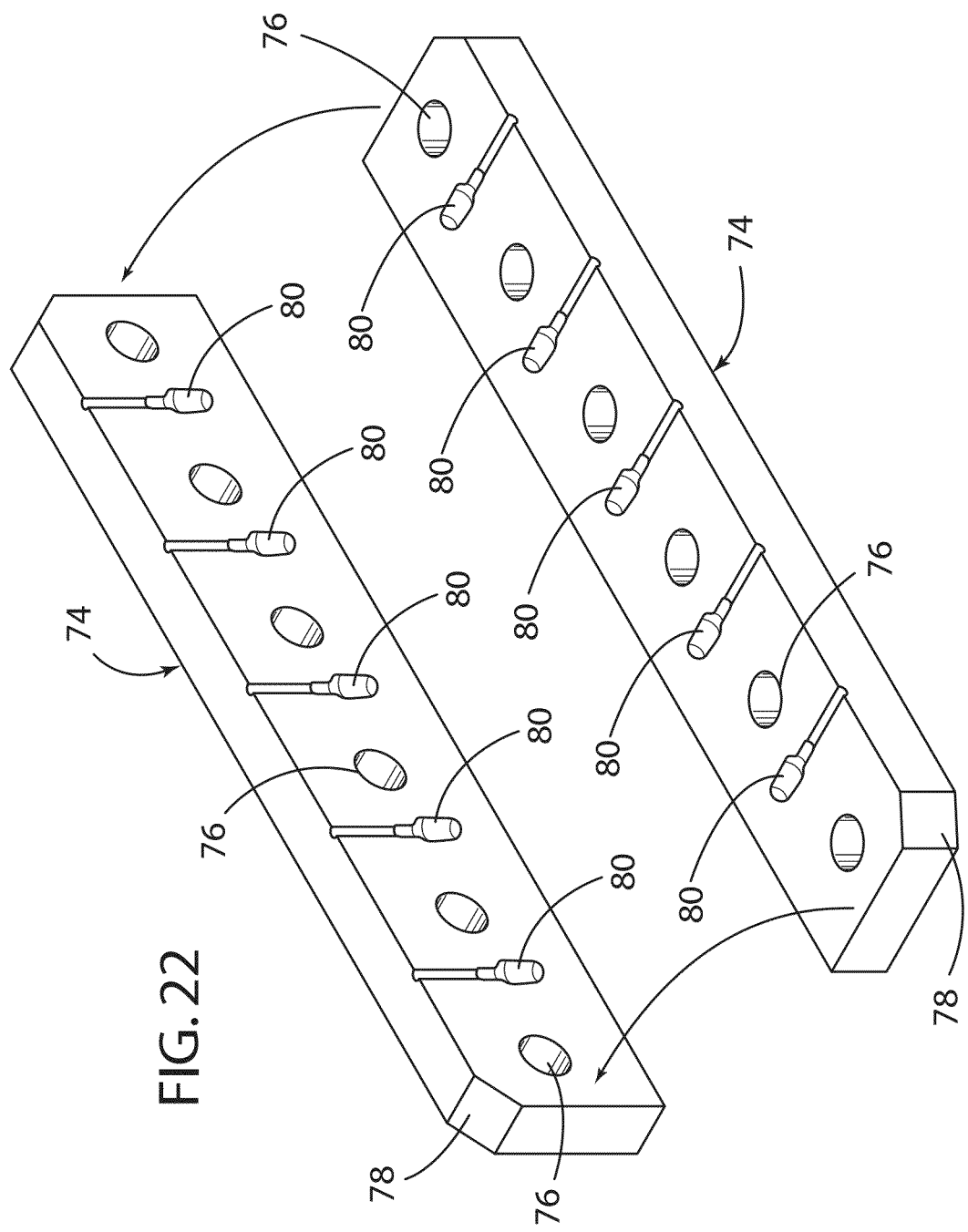

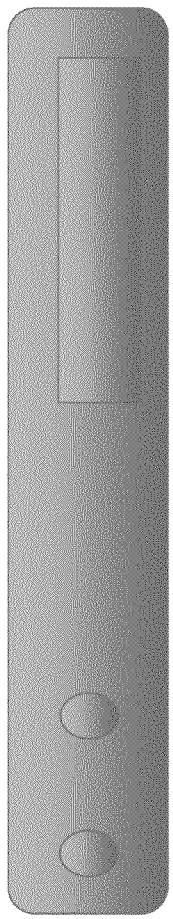
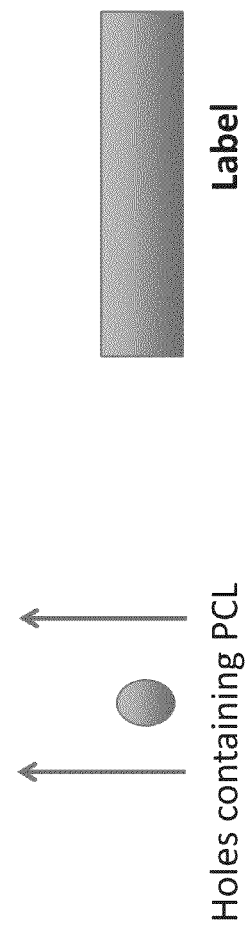
Label
Holes containing PCL
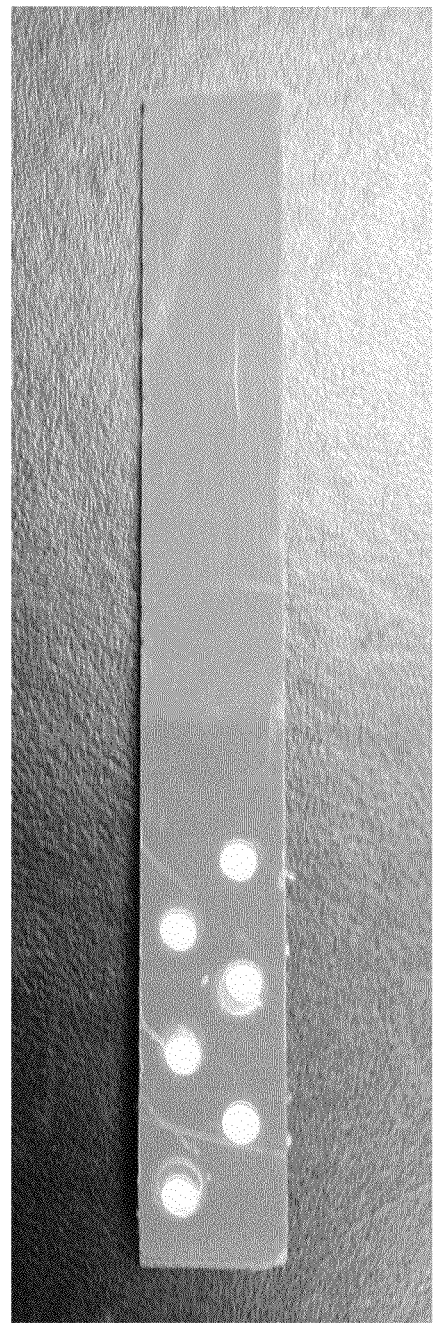
A.
B.
Figure 26

SEQUENCE LISTING

<160> NUMBER OF SEQ ID NOS: 2

<210> SEQ ID NO 1
<211> LENGTH: 6
<212> TYPE: PRT
<213> ORGANISM: Bombix mori

<400> SEQUENCE: 1

Gly Ala Gly Ala Gly Ser
1               5

<210> SEQ ID NO 2
<211> LENGTH: 5
<212> TYPE: PRT

-continued

```
<213> ORGANISM: Homo sapiens

<400> SEQUENCE: 2

Gly Val Gly Val Pro
1               5
```

BIOLOGIC SAMPLE COLLECTION DEVICES AND METHODS OF PRODUCTION AND USE THEREOF

FIELD OF THE INVENTION

Collection devices, kits and methods related to biologic sample collection and more particularly collection devices, kits and methods related to nucleic acid sample collection using a hydrophilic swab matrix are described herein.

BACKGROUND

Collection of biological samples for forensic identification, diagnostic applications, and the like, is a critical first step in the process of analyzing such samples. Current practice in the art typically involves swabbing an individual or area of interest containing deoxyribonucleic acid (DNA) with a cotton swab and subsequently extracting DNA from material (in most cases nucleated cells) from the swab. While recent advances in quality assurance allow for cotton swabs that are DNA-free and of uniform quality, these advances do not address the basic limitation of low DNA yield from cotton swabs, such as when used for forensic applications. Further, the quality of DNA extracted from cotton swabs can be inconsistent.

Accordingly, devices and methods for increasing DNA yield and quality from a sample collection device are desired. Such devices and methods could greatly increase the number of samples that could provide desired information.

SUMMARY

Accordingly, one or more of the embodiments presented herein provide collection devices, kits and methods related to biological sample collection and more particularly, collection devices, kits and methods related to DNA sample collection using a hydrophilic swab matrix having a synthetic component. Biologic sample collection devices are used to take samples from a variety of sources for applications such as forensic and diagnostic purposes involving identification of sample material by testing of extracted nucleic acids (e.g., DNA). Testing can include, for example, obtaining a genetic profile, and comparing it to reference samples. Success of the identification process relies on the quantity and quality of the DNA extracted from the samples obtained on the collection devices. A biologic sample collection device as described herein takes up samples efficiently, and also releases a high yield of DNA (which can be analyzed by one or more various methods or assays known in the art). Furthermore, a biologic sample collection device as described herein lacks materials that impede steps in preparation of the sample or in the analysis of the sample or nucleic acids extracted therefrom (e.g., detailed analyses performed to obtain DNA profiles suitable for unambiguous identification of the sample donor). The manufacture and testing of innovative and improved biologic sample collection devices and kits, as well as uses thereof, are the subject of the present application.

Herein are described biologic sample collection devices made from synthetic materials and from natural substances used either alone or in mixtures formulated to optimize one's ability to collect samples and release nucleic acids (e.g., DNA) from the collected samples. Samples include any nucleic acid-containing biologic material such as all body fluids, nucleated cells obtained by various means and material taken in forensic investigations that may include cells shed in fingerprints. Samples may be those obtained directly from a subject (e.g., a human subject) or those indirectly obtained from a subject (e.g., samples that have been processed in some way prior to obtainment from the subject, samples left at a crime scene, etc.). In one example, the synthetic polymer polycaprolactone (PCL) is used to form heads for swabs designed to collect samples for nucleic acid (e.g., DNA) analyses used for identification of the sample donor (e.g., sequencing DNA from the sample to identify the individual from whom the sample was obtained or originated). The configuration of the swab varies with its intended use and may include numerous sizes and shapes. In the experiments described herein, yields of DNA obtained with the biologic sample collection devices described herein were shown to be superior to those obtained in controlled comparisons using cotton swabs as a collection means.

The synthetic materials to be used in collection devices are in some cases not sufficiently absorbent or hydrophilic to give optimum collection. Treatments to render the materials more hydrophilic and tests to assure success of the treatment are applied to collection devices. These may include changes in the manufacturing process or in the composition of the material such as by copolymerization of materials, addition of absorbent fibers in the manufacture, etc. Properties of the biologic sample collection device may also be changed by post-manufacturing treatment of the collection device. In one example, the PCL swab is treated under carefully controlled conditions with an aqueous base, then neutralized, either by water washing or exposure to acid, and dried. Water uptake by the treated collector is markedly improved over the original non-treated product as shown by qualitative and quantitative measurements as described in the Examples below.

Ease of operator use is aided by the assembly of the biologic sample collector into its own plastic container. The entire assembly is sterilized and rendered nucleic acid (e.g., DNA, RNA)-free by any suitable means or process (e.g., exposure to ultraviolet radiation at an intensity and time that destroys any nucleic acids on the collector). The sterilization process also preferably kills any microorganisms present. The plastic container keeps the collector sterile and DNA-free prior to use. In one embodiment, the biologic sample collection device is housed within a plastic container and is operably connected to a cap that is used to seal the biologic sample collection device within the plastic container. In this embodiment, assembly of the biologic sample collection device handle (referred to below as a carrier) into the cap of the container allows samples to be taken by a user or operator holding the biologic sample collection device by the cap; this avoids the user or operator touching the handle of the collector. After sample acquisition, the biologic sample collection device is placed back into the container where the fit of the cap prevents the swab tip from touching the interior (e.g., sides, tip) of the container to avoid losing any sample by contact with the interior of the container. Although such a container will generally be plastic, any suitable material(s) (e.g., glass) can be used.

Release of DNA from standard cotton swabs has been shown to seldom yield higher than 20% of the actual amount present in the sample. Biologic sample collection devices prepared according to the methods described herein routinely yield 80% of the sample's DNA as shown by controlled experiments. An important factor in obtaining a high yield of DNA from biological samples is the ability of the swab to release the material and the extracted DNA into extraction reagent solutions. The fact that the hydrophilic, soluble PCL portion of the biologic sample collection device (e.g., the PCL matrix) dissolves (is solubilized) in most of the commonly used extraction solutions facilitates high yields of DNA.

Because the goal of the biologic sample collection device in some embodiments is to obtain a useable genetic profile of the individual or subject from whom the sample was directly or indirectly obtained, the quality of DNA obtained and its suitability for subsequent testing is important. The biologic sample collection devices described herein acquire sufficient sample and yield sufficient DNA to allow standard analyses to be performed. This ability was tested using standardized tests, which include DNA extraction with commonly used commercial kits followed by amplification and analysis of areas of interest for genetic profiles used in forensics applications. The biologic sample collection devices as described herein that were tested performed better than comparison products such as cotton swabs in these tests.

In many applications, the collected sample is not analyzed immediately upon acquisition. An identification means to assure that the collector and the sample can be processed without danger of losing the sample information is typically attached to or included in a biologic sample collection device as described herein. The use of bar codes or QR codes placed on the device at the time of manufacture is one example of a means of retention of sample identity, and in such embodiments, the data linking the collector information with the sample is typically secure. Another embodiment of collecting a biologic sample involves the use of an radio-frequency identification (RFID) tag that can be read within reasonable proximity without having to scan all samples in a collection and that can allow additional information about the sample to be added at the time of collection. A passive RFID tag attached to the biologic sample collection device (or to the cap to which the biologic sample collection device is attached per the description above) can be used, and guarantees that sample information and the collected sample cannot be separated. Examples of sample information include date, time, person, location, collector, case number, and combinations thereof.

Accordingly, described herein is a biologic sample collection device including soluble and hydrophilic PCL coupled to a carrier, wherein at least a portion of the PCL solubilizes when exposed to a nucleic acid extraction reagent. The PCL can be copolymerized with at least one agent, e.g., acrylamide, polylactide, polyglycolide, polydioxanone, poly N-isopropylacrylamide, polyurethane, a polyester other than PCL, etc. Typically, the biologic sample collection device has been sterilized, and the PCL has been treated with a base having a pH greater than 8 (e.g., NaOH, NaHCO$_3$, KOH, Na$_2$CO$_3$, and CA(OH)$_2$) and a neutralizing agent for increasing hydrophilicity. In one embodiment, the PCL is coupled to a carbohydrate trehalose derivative group. In another embodiment, the PCL is coupled to at least one protein (e.g., antibody, silk, collagen, fibrin and elastin). The carrier can include one or more of: an identifying label, a radio-frequency identification (RFID) tag, and a bar code. The carrier can include a semi-rigid or rigid member (e.g., a material such as metal, plastic, polymer, wood, glass, or a combination thereof). In some embodiments, the biologic sample is a human buccal sample. In some biologic sample collection devices, the PCL is contained within at least one aperture (e.g., two or more apertures) disposed in the carrier. In such an embodiment, the at least one aperture can be disposed at a first end of the carrier, and an identifying label can be disposed at a second end of the carrier.

Also described herein is a kit for collecting at least one biologic sample. The kit includes: at least one biologic sample collection device including soluble and hydrophilic PCL coupled to a carrier, wherein at least a portion of the PCL solubilizes when exposed to a nucleic acid extraction reagent; and packaging. A kit can further include instructions for use and at least one of: a nucleic acid extraction reagent; a nucleic acid labeling reagent; and a set of reagents for nucleic acid amplification. The packaging can include, for example, a polymer laminate or plastic container. In some embodiments, the kit includes a plurality of biologic sample collection devices. In such embodiments, each biologic sample collection device of the plurality of biologic sample collection devices can be individually packaged (or a plurality of biologic sample collection devices can be packaged within one container or package). In one example, packaging includes: a first container including a rigid housing and a cap to which the biologic sample collection device is attached, the biologic sample collection device positioned in the interior of the housing such that when the cap is operably attached to the housing, the biological sample collection device does not contact the interior of the housing; and a second container in which the first container and the biologic sample collection device are contained. In one example, the first container is plastic and the second container is a plastic bag. In a kit, the PCL can be contained within at least one aperture (e.g., two or more apertures) disposed in the carrier. The at least one aperture can be disposed at a first end of the carrier, and an identifying label can be disposed at a second end of the carrier. The PCL can be copolymerized with at least one agent such as: polylactide, polyglycolide, polydioxanone, acrylamide, poly N-isopropylacrylamide, polyurethane, and a polyester other than PCL. Typically, the biologic sample collection device has been sterilized, and the PCL has been treated with a base having a pH greater than 8 (e.g., NaOH, NaHCO$_3$, KOH, Na$_2$CO$_3$, and CA(OH)$_2$) and a neutralizing agent for increasing hydrophilicity of the PCL. The carrier can include one or more of: an identifying label, an RFID tag, a bar code, and an identifying label.

Further described herein is a method of producing a biologic sample collection device as described herein. The method includes the steps of: providing a solution of solubilized PCL; submersing a carrier at least once into the solubilized PCL solution such that the solubilized PCL solution coats the carrier; subjecting the solubilized PCL solution-coated carrier to treatment with a base having a pH greater than 8 and a neutralizing agent under conditions that result in soluble and hydrophilic PCL coupled to the carrier; and sterilizing the soluble and hydrophilic PCL-coupled carrier such that the soluble and hydrophilic PCL-coupled carrier is free of nucleic acids, resulting in a biologic sample collection device including soluble and hydrophilic PCL coupled to the carrier, wherein at least a portion of the PCL solubilizes when exposed to a nucleic acid extraction reagent. The carrier can be submersed into the solution of solubilized PCL using a fabricated mold. Examples of bases include NaOH, NaHCO$_3$, KOH, Na$_2$CO$_3$, and CA(OH)$_2$. Sterilizing the soluble and hydrophilic PCL-coupled carrier and rendering it free of nucleic acids can include, for example, exposing the soluble and hydrophilic PCL-coupled carrier to UV radiation. The method can further include copolymerizing the PCL with at least one of: polylactide, polyglycolide, polydioxanone, acrylamide, poly N-isopropylacrylamide, polyurethane, and a polyester other than PCL. The method can further include adhering to or coupling to the carrier at least one of: an RFID tag, a bar code, and an identification label.

Still further described herein is a method of extracting nucleic acids from a biologic sample collected by a biologic sample collection device as described herein. The method includes the steps of: contacting the biologic sample (e.g., human buccal sample) and the biologic sample collection device with at least one nucleic acid extraction solution under conditions such that the PCL is solubilized or dissolved, resulting in a solution including nucleic acids separated from the biologic sample collection device; and extracting the nucleic acids from the solution. The step of contacting the biologic sample and the biologic sample collection device with at least one nucleic acid extraction solution can include immersing the biologic sample and the PCL in the at least one nucleic acid extraction solution (e.g., an extraction solution containing at least one proteolytic enzyme). In the method, generally about 50% to about 95% of the nucleic acids from the biological sample are extracted from the biological sample. The carrier can include an RFID tag and the method can further include obtaining information (e.g., date, time, person, location, collector, and case number) from the RFID tag.

Additionally described herein is a method for collecting a biologic sample. The method includes the steps of: contacting a biologic sample collection device as described herein with a biologic sample such that the biologic sample is reversibly adhered to the PCL; contacting the biologic sample collection device and the biologic sample with at least one nucleic acid extraction reagent under conditions such that the PCL is solubilized and the sample is separated from the biologic sample collection device; and collecting the separated sample. The method can further include extracting nucleic acids (e.g., DNA) from the separated sample.

In another method of producing a biologic sample collection device as described herein, the method includes the steps of: providing a solution of solubilized PCL; forming at least a first flat sheet of solubilized PCL; subjecting the at least first flat sheet of solubilized PCL to treatment with a base having a pH greater than 8 and a neutralizing agent under conditions that result in soluble and hydrophilic PCL that solubilizes when exposed to a nucleic acid extraction reagent; coupling the at least first sheet of soluble and hydrophilic PCL to a carrier; and sterilizing the soluble and hydrophilic PCL-coupled carrier such that the soluble and hydrophilic PCL-coupled carrier is free of nucleic acids, resulting in a biologic sample collection device including soluble and hydrophilic PCL coupled to the carrier, wherein the soluble and hydrophilic PCL is a flat sheet, and at least a portion of the soluble and hydrophilic PCL solubilizes when exposed to a nucleic acid extraction reagent.

Unless otherwise defined, all technical terms used herein have the same meaning as commonly understood by one of ordinary skill in the art to which this invention belongs.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

By the phrase "modified PCL" is meant any PCL that has been treated or modified such that the hydrophilicity of the PCL is increased and/or such that one or more surface features of the PCL have been modified (e.g., chemical and/or physical modifications). Examples of surface features include texture (e.g., roughness, smoothness), holes, dimples, channels, protrusions and other irregularities. Any suitable treatment methods, including chemical or physical treatments, for increasing hydrophilicity and/or modifying surface features of PCL can be used. For example, PCL can be subjected to (treated with) a base (e.g. having a pH above 8). Examples of bases include $NaHCO_3$ and NaOH.

As used herein, the phrase "soluble and hydrophilic PCL" means polycaprolactone (PCL) that has been treated in some manner to make it absorb water and to become soluble in nucleic acid extraction reagents (e.g., DNA extraction solutions).

As used herein, when referring to a biologic sample collection device, the term "carrier" refers to any structure or implement to which PCL is coupled, adhered, or disposed on or within. A carrier as described herein assists man or machine in exposing PCL to a biologic sample, and subsequent processing, e.g., hand held or "machine-held." Examples of carriers include rigid and semi-rigid materials, such as wood, plastic, glass, rubber, and polymers.

By the phrase "nucleic acid extraction reagent" is meant any reagent (e.g., solution) that can be used to obtain a nucleic acid (e.g., DNA) from biological materials such as cells, tissues, bodily fluids, microorganisms, etc. An extraction reagent can be, for example, a solution containing one or more of: a detergent to disrupt cell and nuclear membranes, a proteolytic enzyme(s) to degrade proteins, an agent to inhibit nuclease activity, a buffering compound to maintain neutral pH, and chaotropic salts to facilitate disaggregation of molecular complexes.

As used herein, the term "copolymerized" refers to using two or more monomeric units to form a polymer with inclusion of both in some random (e.g., AABABBBAA-BAAABBBBA) or defined order (such as, e.g., AAABAAA-BAAAB or ABABABAB or ABAABAABAABAABAABA). For example, when referring to PCL that is copolymerized with at least one agent such as, e.g., L-lactic acid, the copolymer formed is a poly caprolactide called poly-L-lactic-co-ϵ-caprolactone.

By the phrase "PCL composite solution" is meant PCL dissolved in a solvent. A PCL composite solution can be used to prepare a biologic sample collection device as described herein by filling in molds or adding between glass, plastic or metal plates, for example, to make sheets of PCL. Glacial acetic acid is one example of a solvent for PCL that may be used.

The phrase "under conditions that result in soluble and hydrophilic PCL coupled to the carrier" encompasses any suitable methods and steps for treating PCL, a solubilized PCL solution, or a solubilized PCL solution-coated carrier that contribute to an increase of hydrophilicity and/or solubility during preparation of a biologic sample collection device as described herein. Conditions may include, for example, treatment of a solubilized PCL solution (e.g., a solubilized PCL solution-coated carrier) with a base prior to neutralization, one or more drying steps, one or more washing steps, etc.

As used herein, the phrase "flat sheet of solubilized PCL" means a generally flat and thin (e.g., about ⅛ to about ⅜ inches thick) piece or portion of solubilized PCL. A flat sheet of solubilized PCL can be of any suitable shape, including, for example, square or rectangular.

By the term "neutralizing agent" is meant any reagent (e.g., a solution, liquid, etc.) that when contacted with PCL, for example, brings the pH of the PCL to a neutral pH. Nonlimiting examples of neutralizing agents include water and acidic solutions.

The terms "patient," "subject" and "individual" are used interchangeably herein, and mean a mammalian (e.g., human, rodent, non-human primates, canine, bovine, ovine, equine, feline, etc.) subject to obtain a biologic sample from.

The phrases "isolated" or biologically pure" refer to material which is substantially or essentially free from components which normally accompany it as found in its native state.

The term "antibody" is meant to include polyclonal antibodies, monoclonal antibodies (mAbs), chimeric antibodies, humanized antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques.

The term "sample" is used herein in its broadest sense. A sample including polynucleotides, polypeptides, peptides, antibodies and the like may include a bodily fluid, a soluble fraction of a cell preparation or media in which cells were grown, genomic DNA, RNA or cDNA, a cell, a tissue, skin, hair and the like. Examples of samples include saliva, serum, blood, urine, buccal cells, and plasma.

Other features will become more apparent to persons having ordinary skill in the art to which the package pertains and from the following description and claims. Although devices, kits, and methods similar or equivalent to those described herein can be used in the practice or testing of the present invention, suitable devices, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

The above and other aspects, features and advantages of the present embodiments will be more apparent from the following more particular description thereof, presented in conjunction with the following figures.

FIGS. 15-21 are perspective views of several embodiments of a biologic sample collection device as described herein.

FIG. 22 is an exploded perspective view of one embodiment of a mold for producing a biologic sample collection device as described herein.

FIG. 26 shows one embodiment of a biologic sample collection device as described herein. FIG. 26A is a schematic illustration of a biologic sample collection device, including holes that contain PCL and a label (e.g., an identifying label). FIG. 26B is a photograph of a biologic sample collection device having holes (apertures) in which PCL is disposed or deposited.

Corresponding reference characters indicate corresponding components throughout the several views of the drawings.

DETAILED DESCRIPTION

Figure 1:
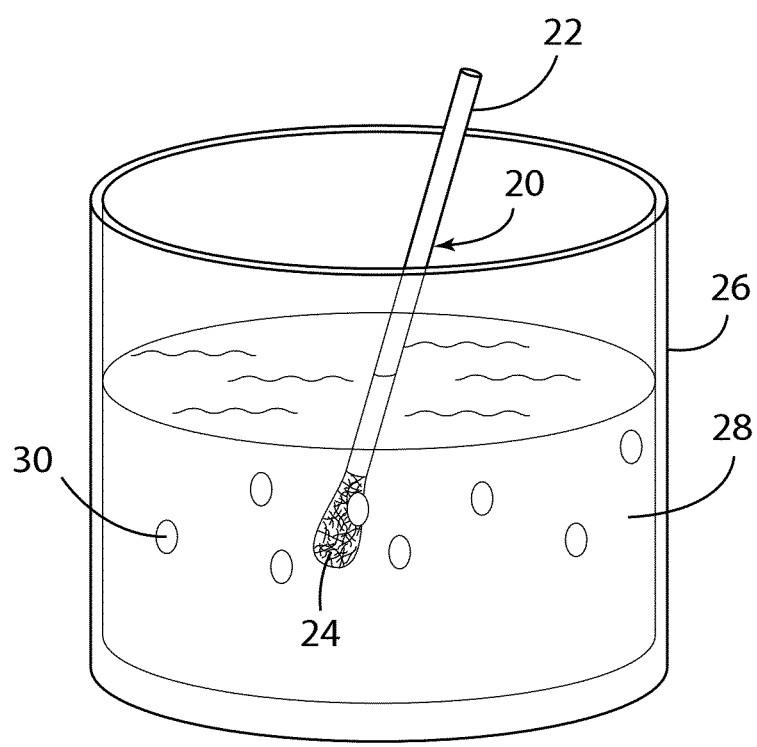
FIG. 1 is a perspective view of a biologic sample collection device as described herein in a biological sample extraction system.

Despite advances in the art to improve the quality, cost and efficiency of biological specimen collection devices, such as those made from cotton, further improvements are desirable. Accordingly, one or more of the embodiments presented herein provide collection devices (and methods of production and use thereof) related to biological sample collection and more particularly, biologic sample collection devices and methods related to DNA sample collection involving a biologic sample collection device having a hydrophilic swab matrix that includes a synthetic component. In a typical embodiment, the swab includes a modified PCL as the synthetic component. The biologic sample collection devices, kits and methods described herein are used to collect a biologic sample (e.g., blood, buccal cells, etc.) and to enable extraction of nucleic acids (e.g., DNA) from that biologic sample so that the nucleic acids can be analyzed (e.g., sequencing and subsequent analyses of DNA). Generally, as referred to herein, "sample release" is the separation from or release of a biologic sample from a biologic sample collection device as described herein. Specifically, "sample release" usually refers to separation from or release of the biologic sample from the soluble and hydrophilic PCL component of the biologic sample collection device.

The following description is not to be taken in a limiting sense, but is made merely for the purpose of describing the general principles of exemplary embodiments. The scope of the embodiments should be determined with reference to the claims. Such biologic sample (e.g., biological specimen) collection devices and methods can be useful in biomedical applications and nucleic acid (e.g., DNA) forensics.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

To increase efficiency of sample release and to assure high quality of the nucleic acids (e.g., DNA) obtained, the present embodiments provide alternatives to cotton as a swab material. The present embodiments provide materials that absorb biological samples efficiently, yet are soluble in extraction reagents (e.g., extraction buffers). This results in high yields of DNA suited to DNA profiling using, for example, short tandem repeats (STRs). In the embodiments described herein, synthetic materials in various combinations show superiority to cotton in the amount of DNA from control blood samples obtained using standard commercially available DNA extraction kits. Using such kits, optimal compatibilities between the biologic sample collection devices described herein (at times referred to herein as "swabs") and the extraction process can be determined. In some embodiments, the synthetic swab materials dissolve completely in an extraction buffer. A variety of swab compositions for forensic applications can be designed, developed, optimized and validated.

Accordingly, in one embodiment, an element in the maximization of DNA yield can be a swab head that dissolves in DNA extraction medium, thus preventing retention of absorbed sample by the swab head. In another approach, improved tracking for a biological sample collection device is provided by use of at least one unique identifier device including an RFID tag. Such a device can be situated in and/or on the biologic sample collection device itself, on or in the packaging thereof, on a container thereof (e.g., a specimen collection tube), and or on the cap of a container for a biologic sample collection device as described herein. These devices are paired with software that can store a variety of detailed information concerning the nature of the sample taken. In another approach, a kit is provided for use in forensic analyses that can perform the initial steps subsequent to sample collection (such as sample preparation and/or analysis) and also to signal a user that sufficient DNA has been obtained to allow complete analysis of the sample.

The biologic sample collection devices described herein are made from materials that do not react with a collected sample or specimen in unexpected ways, unless configured to do so, and preferably are not effected by exposure to altered levels of various environmental conditions, such as elevated ultraviolet (UV) light. In a typical embodiment, sample/specimen profile analysis data is reportable in a format usable with the Combined DNA Index System (CODIS). CODIS is an FBI funded database that stores DNA profiles created by US federal, state, and local crime laboratories. CODIS provides a searchable database of DNA profiles to assist in the identification of suspects in crimes. The biologic sample collection devices as described herein are able to be manufactured in a scalable fashion (e.g., large scale) to provide consistent and reliable swabs.

An additional challenge to biologic sample collection applications is the assurance that the collected sample will yield sufficient DNA for subsequent analyses (e.g., typing procedures needed to establish the identity of the individual who was the sample source). Using conventional techniques, this assurance is not available until the DNA from the specimen is amplified and the product is tested against known quantities of DNA supplied as controls in the amplification kits. The present embodiments can provide a reagent set that yields information on the quantity of DNA obtained at the collection site. This allows collection of additional samples should the amount be found inadequate. In one embodiment, a biologic sample collection device kit is provided that allows initial steps of the analytic process to begin in the field and to give an indication of the quantity of DNA obtained. Such a kit can include a biologic sample collection device packaged with DNA extraction reagents in lyophilized form. In this embodiment, a rapid amplification of DNA follows subsequent to extraction. Following the amplification of the extracted DNA, a colorimetric indicator can be used as a signal that there is (or is not) adequate DNA for complete analysis. This colorimetric indicator can be a DNA-indicating dye included in the reagent, or alternatively, on an impregnated paper to which a drop of solution is added. Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

Figure 2:
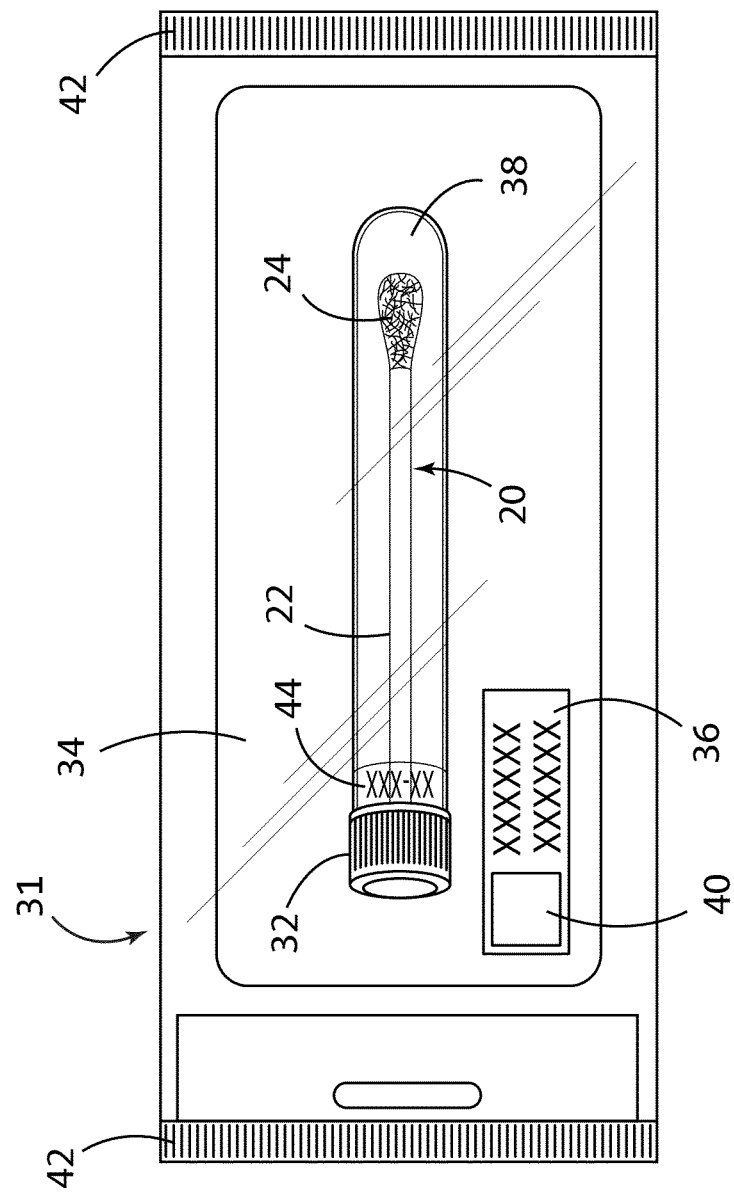
FIG. 2 is a plan view of a biologic sample collection device kit as described herein.
Figure 24:
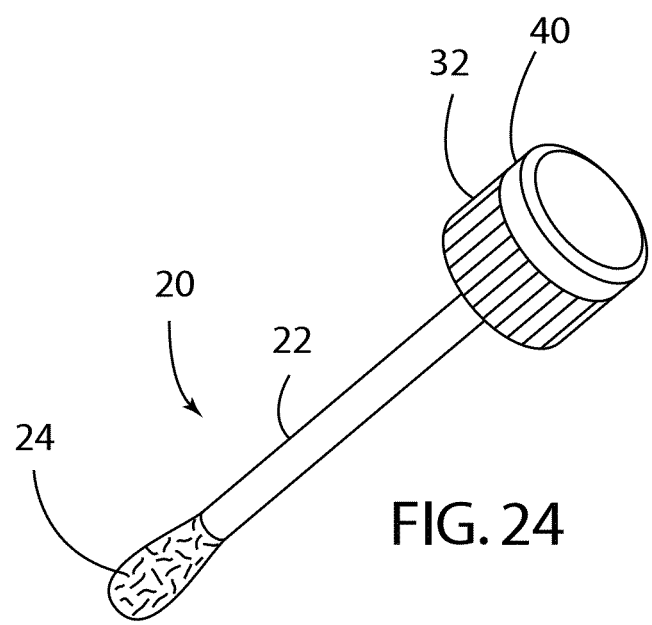
FIG. 24 is a perspective view of a biologic sample collection device as described herein.
Figure 25:
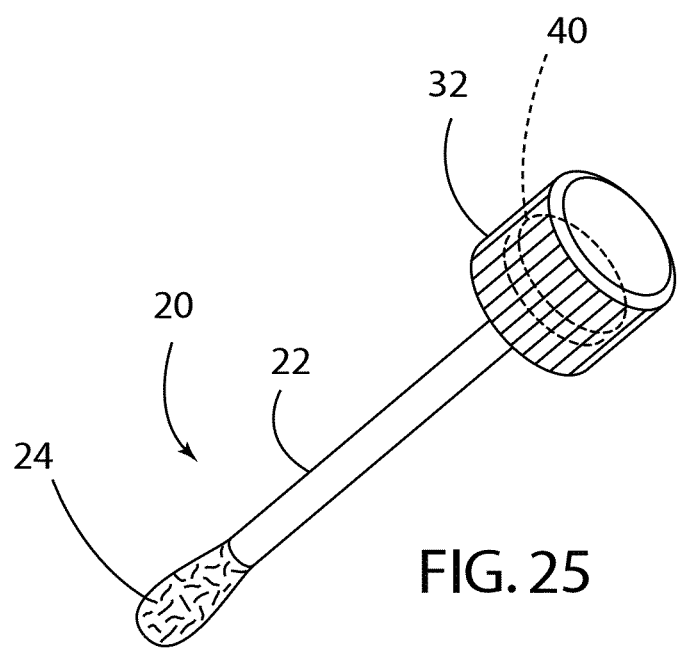
FIG. 25 is a perspective view of a biologic sample collection device as described herein.

Turning now to the figures, there is shown generally in FIG. 1 a biologic sample collection device as described herein positioned in a biological sample extraction system. Shown in FIG. 2 is one embodiment of a biologic sample collection device kit. FIG. 1 generally shows a biologic sample collection device 20 having a soluble and hydrophilic PCL 24 attached to a carrier 22. As shown in FIG. 1, DNA 30 from soluble and hydrophilic PCL 24 can be extracted while in an extraction solution 28 (such as are commercially available to allow DNA profiling) disposed in an extraction system container 26. FIG. 2 illustrates one embodiment of a biologic sample collection device kit generally indicated at 31. In this embodiment, biologic sample collection device 20 is contained or disposed within a first container 38, and the biologic sample collection device includes a cap 32 which can be operably attached to the first container 38 such that the carrier and soluble, hydrophilic PCL 24 are sealed within the first container 38. In FIG. 2, a second container 34 envelops and contains the biologic sample collection device 20 and the first container 38. Kit 31 can be sealed in a hermetically sealed second container (e.g., film package) 34 made from, for example, a polymer laminate. As shown, second container 34 can be sealed at its ends 42, though other approaches, such as a three or even four sided seal are possible. Second container 34 can have label 36 having identifying indicia, which may include a bar code, an RFID tag 40, or both a bar code and an RFID tag. It is noted though that RFID tag 40 could also be positioned on carrier 22 of collection device 20 or first container 38. Also, as shown in the figures, RFID tag 40 can be positioned on top of the cap (e.g., seal) 32 (FIG. 24) or within the cap (e.g., seal) 32 (FIG. 25). In these last two embodiments, the identifier and the sample are not separable prior to analysis. A biologic sample collection device or kit as described herein can include one or more of: an RFID tag, a bar code, and a label (e.g., two or more of an RFID tag, a bar code, and a label; all of an RFID tag, a bar code, and a label).

The importance of specimen identification, whether by indicia, RFID tags, bar codes, and the like, and combinations thereof, cannot be understated. Sample collection devices, such as in forensic applications, are used to obtain samples of biological materials for subsequent analyses that serve to establish the identity of the sample source by subsequent analytic steps. The sample collection device may be subject to analyses immediately or it may be stored for some period of time prior to analysis. Often multiple samples must be taken (for example at a crime scene). In this instance the samples may not be analyzed for long periods of time because of a backlog in the laboratory, or the need to send samples for tests not available near the scene of collection. Therefore, it is important that certain identification criteria accompany the sample. Current procedures in the art for providing a clear and secure means to locate and identify the sample at any stage in the process depend mainly on a bar coded identity of the sample collected on the device and handwritten information on packets in which samples are placed upon collection. The present embodiments provide improvements to the accuracy, quality and quantity of sample information handling.

In addition to the standard barcode or quick response ("QR") code carrying a manufacturer's information and identifier, as is known in the art, the present embodiments provide a passive RFID label (an RFID tag) used to tag the device. The RFID tag can be imprinted with information, such as a bar or QR code. This manufacturer-supplied information can include lot and serial number to unambiguously identify the collection device. In one embodiment, the RFID tag can be further programmed to include user-supplied data that relates to the sample taken in a specific manner. This provides an additional advantage over bar codes that use a simple scanning device to allow users to scan collections of samples in a storage area, such as a refrigerator or freezer. Here, use of a programmable RFID tag allows obtaining of information (both user and manufacturer supplied) on the tag without removing and scanning each unit individually as with samples having only bar or QR codes.

Most instruments used for analyses of the samples retrieved from a biologic sample collection device described herein can also be programmed to read the tag and thus incorporate all information along with the results for easy and secure display. The inseparability of the sample and its detailed identity and the ability to locate specific samples with relative ease can greatly aid forensics applications where, for example, a chain-of-custody needs to be documented to be admitted into evidence in court proceedings. An example of how a programmable RFID tag can be implemented in forensic specimen collection can be initiated as follows. Upon completion of manufacture, a given lot or batch of biologic sample collection devices or kits as described herein (e.g., biologic sample collection swabs) is assigned a lot number which includes an identity code of the product (for example P120302) and each unit is given a serial number such as 1001 to 9999. These identifiers along with additional company-supplied data are programmed into the RFID tag and additionally imprinted on a bar or QR code printed on the tag. These labels are printed at the time of manufacture using a commercially available printer.

When a user collects a sample with a biologic sample collection device as described herein, in one approach they may add additional information of their own choosing to the RFID tag by use of a portable programming instrument. This user-supplied data may include, but is not limited to: the circumstances for taking the sample (offense, victim, suspect), the place and time at which the sample was taken, the source of the sample, the identity of the person(s) taking the samples, and the like. These data can be used to establish the authenticity and origin of the samples and, with a clear record of the chain-of-custody for the sample, represent information for the sample to be admitted into evidence in court proceedings. Using conventional methods, sample/specimen identification is either by written record accompanying the sample collection device or by a barcode present on the container in which the device is stored awaiting analysis. Unless the identifying barcode is inseparable from the collector, problems may occur from separation of sample from this identifier. Typically, the bar or QR coded information yielded upon scanning cannot be expanded after its initial printing so no user-specific information is included.

In a typical embodiment, once entered, no data on the RFID tag may be erased or altered. It is noted that as technology improves, the amount of information present on the RFID tag will increase. At present, a commercially available and economical RFID tag can have the manufacturer's identifier and an additional 60-70 characters from the user. RFID tags now in the testing phase have 10 times that capacity. Use of RFID tags is known in the art and is described, for example, in U.S. Pat. No. 7,978,074.

The exact location of the tag on the collection device may vary and the signal from the tag is preferably readable within at least 5 feet of the tag. If the tag is in a visible place the bar or QR code can also be scanned to provide further verification of the identity of the device or kit. To enhance reliability of the RFID tag, it can be attached to a biologic sample collection device or kit with an adhesive that renders the tag useless if accidental or intentional removal is attempted.

Those skilled in the relevant art will appreciate that the embodiments described herein can be practiced with any of various communications, data processing, or computer system devices, including: hand-held devices (including personal digital assistants (PDAs)), wearable computers, cellular or mobile phones, multi-processor systems, microprocessor-based or programmable consumer electronics, network PCs, mini-computers, mainframe computers, and the like. Aspects of the invention described herein may be stored or distributed on computer-readable media, including magnetically or optically readable computer discs, hard-wired or preprogrammed chips (e.g., EEPROM semiconductor chips), nanotechnology memory, biological memory, or other data storage media. Computer-implemented instructions, data structures, screen displays, and other data under aspects of the invention described herein may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme).

First container 38 can be made from a variety of materials such as a glass tube that is closed at one end and configured to receive a biologic sample collection device that includes a cap (e.g., seal) 32 at a second end. The seal formed between cap (e.g., seal) 32 and first container 38 preferably provides a watertight seal in up to two atmospheres of pressure at ambient temperatures (e.g., about 20-25 degrees Celsius). Cap 32 can be made of any suitable material, e.g., rubber, plastic, or other synthetic polymer. First container 38 can also include an identifying label 44. Cap 32 can be connected to carrier 22 using a variety of means such as by a non-reactive glue, a pressure fit into a seal bore (not shown), and the like. The bore to receive the carrier 22 can be a variety of shapes designed to retain a carrier end having a reciprocal shape. In one embodiment of an assembled biologic sample collection device as described herein, the soluble, hydrophilic PCL portion 24 has at least about a 1 mm clearance from the sides of first container 38, but can preferably range from about 1 to 4 mm (e.g., 0.8 mm to 5.0 mm). The soluble, hydrophilic PCL portion 24 is typically also disposed within the first container 38 such that it has a suitable amount of clearance from the tip or bottom (e.g., portion or end opposite the cap 32) of the first container 38, e.g., at least about a 1 mm (e.g., 0.8 mm, 1.0 mm, 1.1 mm, 1.5 mm, etc.) clearance.

Figure 8:
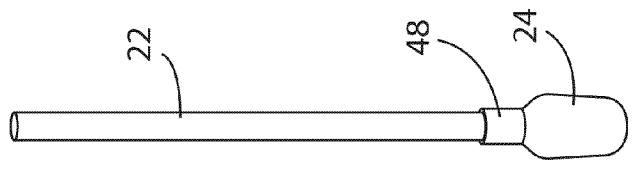
FIGS. 4-8 are perspective views of several embodiments of a biologic sample collection device as described herein.
Figure 5:
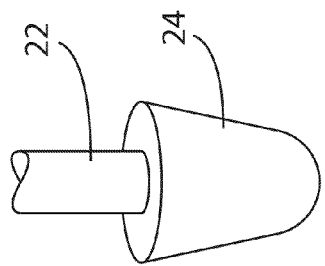
Figure 7:
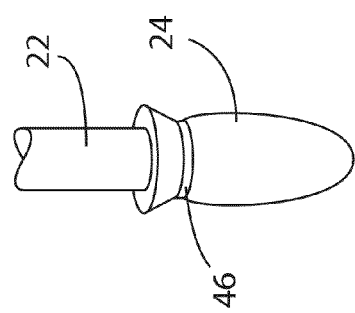
Figure 4:
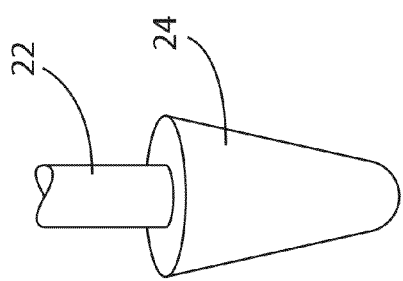
Figure 6:
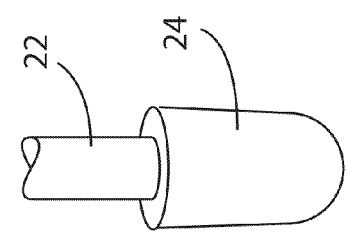

FIGS. 4-8 and 15-21 show non-limiting examples of various shapes and configurations of the soluble, hydrophilic PCL portion 24 of a biologic sample collection device 20. A nonlimiting list of shapes includes: cubes, cuboids, cones, sphere, cylinders, spheroids, prisms, square-based pyramids, triangular-based pyramids, essentially two-dimensional shapes and configurations, etc. Variables affecting shape can include consideration of the sample origin to be collected, manufacturing efficiency, material economy, storage, clearance within first container 38, and the like and combinations thereof. It is noted that even a flat sheet of soluble, hydrophilic PCL 24 as shown in FIG. 21 can be used, e.g., used in filter paper tests in mandated new born screening programs. Also, FIG. 7 shows an optional band 46 to retain soluble, hydrophilic PCL. FIG. 8 shows an additional collar of soluble, hydrophilic PCL 48. It is noted that this type of collar 48 may be the result of overfill during a molding process described herein.

Materials selected for use in a biologic sample collection device preferably provide no or limited adverse affect to targeted biospecimen samples and are easy to handle or use. Such materials (e.g., soluble, hydrophilic PCL) efficiently adsorb samples of various types such as bodily fluids, cells shed from fingerprints, and the like. Such materials should release samples with high efficiency using, for example, commercially available DNA extraction kits. Typically, the material (e.g., modified PCL) added to or disposed on or within the carrier is soluble with no unintended interference with subsequent tests and analyses. Such solubility reduces sample handling and provides a great advantage of being able to go immediately into robotic analytic systems. The biologic sample collection devices described herein have a reasonable cost of manufacturing, yet provide product consistency. PCL is strong, but soft and foamy. It is an easily manufactured and biodegradable polyester with a low melting point of around 60° C. However, PCL has low hydrophilicity (i.e., a low affinity for water; not easily absorbing or dissolving in water). As described in more detail below, the biologic sample collection devices include PCL that has been modified or treated to be soluble and hydrophilic.

PCL is a monopolymer made by a ring-opening polymerization of epsilon caprolactone. Similar polymers are polylactide, polyglycolide or polydioxanone. PCL may be copolymerized with other esters such as polylactide to alter properties. Polymers of acrylamide may also be used, such as poly N-isopropylacrylamide. The addition of derivative groups to the PCL polymerization reaction may be used to change properties of the PCL. For example, the carbohydrate trehalose can be used to enhance DNA stability.

Stability of collected biological samples is critical for accurate analysis and profiling. Results obtained from analyses of the collected samples should be comparable irrespective of the time interval between collection and analysis. Typically, analyses are not performed immediately after sample harvest and there are a number of chemical and biological agents and conditions that can affect the integrity of the sample or of the DNA from it. Insulation from atmospheric conditions by storage in temperature and humidity controlled areas is common to preserve sample integrity. Several methods are known to preserve purified DNA from degradation after primary processing of the samples at the analytical laboratories. As indicated above, a carbohydrate, trehalose, is one of the compounds currently used as a stabilizer for dried DNA during storage. It is most effective when the purified DNA is stored at about of range of −60° C. to −90° C., and preferably about −80° C. or at ambient temperature (e.g., about 18° C. to 25° C.). A possible mechanism of action is that trehalose replaces water molecules lost during desiccation. In one embodiment, trehalose can be mixed with PCL or other swab materials to increase the hydrophilicity of the PCL and, at the same time, give greater stability to the DNA in the sample from the moment of collection.

In another approach soluble, hydrophilic PCL 24 can be impregnated with a bacteriostatic or fungicidal substance to inhibit bacterial growth for samples in storage. Other possible modifications include inhibitors of enzymes (such as DNAse or other nucleolytic enzymes) that can degrade the sample. Such modifications are amenable to any of the considered swab material formulations. In other approaches, soluble, hydrophilic PCL 24 can be modified by coupling a protein to PCL, such as an antibody.

PCL as a swab component is unknown since it typically is not suitable to collect biological samples since hydrophilicity is an important element for a collection swab composition. Accordingly, the PCL as presented herein, is modified to improve its hydrophilicity. Such PCL modification preferably enhances absorbency, sterility and freedom from contaminating DNA. PCL can be modified using any suitable chemical or physical methods. One or more surface features of PCL can be modified (or added) to increase hydrophilicity.

Solutions used in the production of soluble, hydrophilic PCL 24 can be sterilized using filtration where sterility is maintained by handling the assembly and packaging of the product in a clean room environment. Alternatively, a biologic sample collection device (e.g., a swab as described herein) or specimen/sample collection kit can be sterilized using UV or gamma irradiation of the finished packaged product. This procedure can also increase wettability and hydrophilicity of the PCL swab.

PCL for use in the devices, kits and methods described herein can be mixed with several chemicals during manufacture to give varying properties and a desired amount of hydrophilicity. For example, $Ca(Cl)_2$ can be added during a solubilization step of the PCL. As another example, PCL can also be treated with a solution of $Ca(OH)_2$ or NaOH. Both methods can be used to increase the hydrophilicity of the PCL. It is noted though that soluble, hydrophilic PCL 24 can be coupled to and/or copolymerized with a variety of other materials in addition to PCL in various proportions and combinations to yield a biologic sample collection device (e.g., a swab as described herein) with the desired absorbency and solubility. For example, the soluble, hydrophilic PCL can include alginate, silk or other natural fibers.

PCL can also be mixed with several proteins like silk, collagen, fibrin, antibodies, or the like, or various combinations thereof to increase the same. Such proteins can be extracted from natural sources or produced using recombinant organisms expressing the proteins of naturally occurring cloned genes or from synthetic genes. In one approach where the protein is silk, the silk is purified and ground to a fine powder, and then mixed at about 1 to 3 percent weight/volume of the PCL solution. Where the protein is a genetically engineered protein it can have defined properties and expressed in vitro.

Soluble, hydrophilic PCL 24 can also be coupled to a genetically engineered protein with defined properties and that can be expressed in vitro. For illustrative purposes only, in one approach, genes can be synthesized coding for protein sequences containing the repeat found in *Bombix mori* crystalline region of silk (GAGAGS) (SEQ ID NO:1) and the pentapeptide of human elastin (GVGVP) (SEQ ID NO:2) to form proteins of about 60 kDa. Through recombinant DNA technology procedures, the proteins can be expressed and purified from a variety of expression organisms including but not limited to bacterial strains such as *E. coli* or *B. subtilis*, or higher organisms such as fungi, yeasts human cell lines such as CHO, and the like. In the same manner, genes encoding various collagen sequences can be synthesized and purified. These proteins can be shaped into fibers, sponges, and the like.

Additionally, proteins incorporated into soluble, hydrophilic PCL 24 can be designed to contain, interspersed at regular intervals, specific sequences to be utilized in chemical reaction or biological functions. As an example only, such sequences could contain the amino acid Lysine (to introduce an active primary amine) or binding site such as RGD (to bind specific cells).

In one format, the PCL swab may be configured for use in systems that require small sample size in the extraction step of the analytic process. Typically in current usage, a sample is taken by buccal swab onto a paper collector. This collector is then punched to obtain a small (1.2 mm) sample of the paper containing the sample which is placed into the extraction mixture directly. Because the buccal sample is relatively rich in cells from which DNA may be extracted, the small sample suffices to yield material for the analytic process. However, there is a failure rate to the process that may be due to an uneven distribution of cells on the paper. Taking a larger punch from the paper can interfere with downstream steps of extraction and amplification.

A biologic sample collection device (e.g., biologic sample collection swab) tailored for this purpose using PCL is described herein. In this embodiment, the swab handle is plastic (or hard non-porous wood) in a semi-cylinder or flat ovoid shape with one or more holes, dimples, apertures, depressions, etc., into which PCL has been introduced. The biologic sample collection device is used as a collector of buccal cells wherein the PCL areas take up cells with greatest efficiency compared to the hard wood or plastic surrounding material. The PCL contained in the holes is then pushed through the carrier (e.g., swab handle) into a tube containing extraction mix and the process of extraction, amplification and analysis begins. The implement for removing the PCL plugs from the handle resembles a toothpick and is sterile, DNA free and non absorbing. In this embodiment, the fact that the PCL contained in the hole is exposed on two sides of the carrier gives it good accessibility to cells in the sample. Although exposure on two sides is unnecessary, it does allow good access to cells in saliva and makes it easy to remove the PCL by punching it out into a tube, for example. The wetting of the PCL with saliva that occurs in the buccal collection event will facilitate uptake of material into the PCL which is the only absorbent material on the biologic sample collection device. A further advantage is given by the fact that the PCL is soluble in most extraction reagents and does not interfere with analyses allowing a sample larger than the 1.2 mm paper punch to be used.

The PCL used for this purpose may be prepared in sheets and conditioned to be hydrophilic prior to coupling the PCL to a carrier (e.g., introduction into the swab handle). Alternatively, it may be introduced in the liquid form and conditioned (treated or modified) while coupled to a carrier. Co-polymers of PCL and mixes with other materials may be used to maximize uptake of saliva and cells into the PCL portion(s) of a biologic sample collection device as described herein.

In the biologic sample collection device shown in FIG. 26, there are at least two areas into which PCL is introduced. Such a biologic sample collection device may be particularly useful for reference sample collection. In some embodiments, the collected sample or specimen may be taken from only one of these while the other is stored for future use. A label is affixed to the sample with bar or QR code to allow identification of the sample to remain with the material. FIG. 26 shows one embodiment of a biologic sample collection device for reference sample collection, which allows facile collection of cells such as buccal cells, for example.

Figure 3:
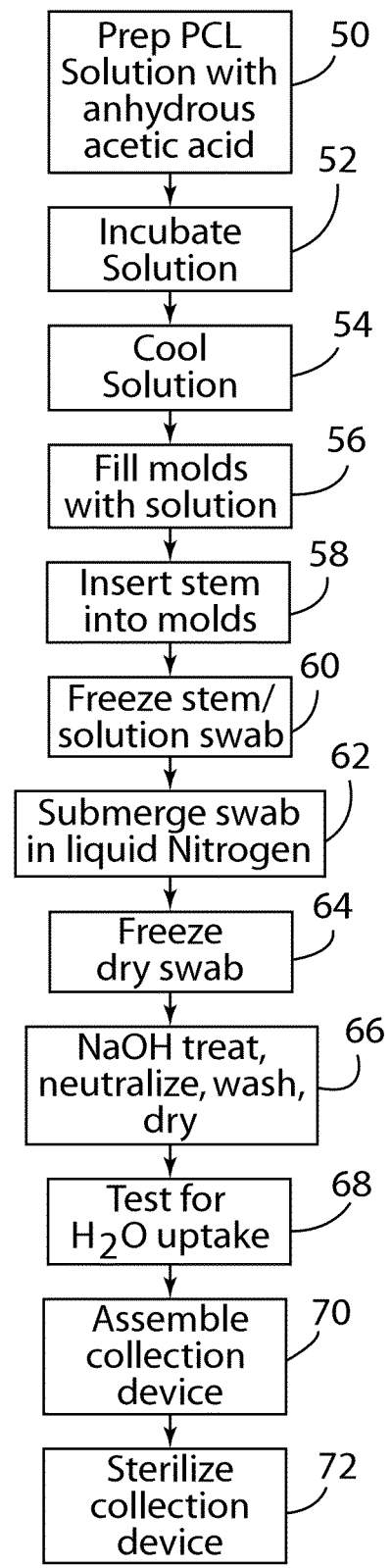
FIG. 3 is a schematic of one example of a method to produce the biologic sample collection device kit of FIG. 2.

Turning now to FIG. 3, there is shown a schematic diagram of one method to produce a biologic sample collection device kit as described herein. It is noted that at ambient temperatures (e.g., between about 20-25 degrees Celsius, with an average of about 23 degrees Celsius) PCL is soluble in a variety of solvents including chloroform, toluene, 2-butanone, dichloromethane, acetone, ethyl acetate, acetonitrile, and the like and combinations thereof. Accordingly, several of these solvents can be used to form the biologic sample collection devices (e.g., biologic sample collection swabs) of the present embodiments, but for illustrative purposes in the method described, PCL is solubilized in glacial acetic acid. Acetic acid is a concentrated vinegar, but it is otherwise a fairly weak acid and not regulated as a carcinogen and therefore not regulated for safety handling. Preferably the pH range of the solvent is about 4-10. This range allows for easier disposal used materials. In short, acetic acid in this pH range allows large scale and economical swab production.

Beginning at step 50, a solution is prepared having a matrix forming material, such as PCL, between about 3 percent and 10 percent (preferably between about 4 percent to 7 percent and most preferably at about 5 percent) weight/volume in the specified solvent, typically glacial acetic acid. Other components can include other co-polymers, silk fiber, synthesized proteins (recombinant proteins structural and functional) and the like. The other co-polymers can include PMMA, LPGA, and the like. Further, trehalose (a tri-saccharide) can also be a component of the solution as well as chitosan, and the like. It is noted though that even as the composition component varies, the overall percent weight/volume as stated above for the matrix forming material is preferably mantained.

Next, at step 52, the solution is incubated. The PCL solution can be delivered to a bath kept at about 60° C. to 70° C. In one approach, the temperature chosen can be about 65° C. with optional stirring, such as for about 2 hours, for usually about 1 to 4 hours of incubation. At step 52, if a solvent other than glacial acetic acid is used, the incubation can be maintained at or near ambient temperature. It is noted that the incubation can occur at room temperature for any bath, but the increased temperature is used to reduce incubation time. At ambient temperature, incubation could take about 24 hours. Stirring also creates homogeneous mixture, so it does not need to be stirred continuously, if at all. Nevertheless, stirring can reduce incubation time and increases homogenicity.

Once incubated, the process can move to step 54, where the PCL solution is cooled at ambient temperature, if needed. As volume increases, it may need to be cooled under temperature control. A heat exchanger can be used to bring temperature to ambient. Stirring could also be used in a temperature controlled environment. In one approach, the incubated solution is allowed to equilibrate to an ambient temperature, such as between about 20-25° C. This step facilitates the handling of the solution and reduces evaporation rate of the solvent thus reducing change in the desired concentration of PCL. This temperature can be different based on the characteristics of the solvent used to generate the PCL solution. This incubation and cooling step is preferably in an enclosed environment so as to minimize changes in percent volumes of the solute.

Figure 9:
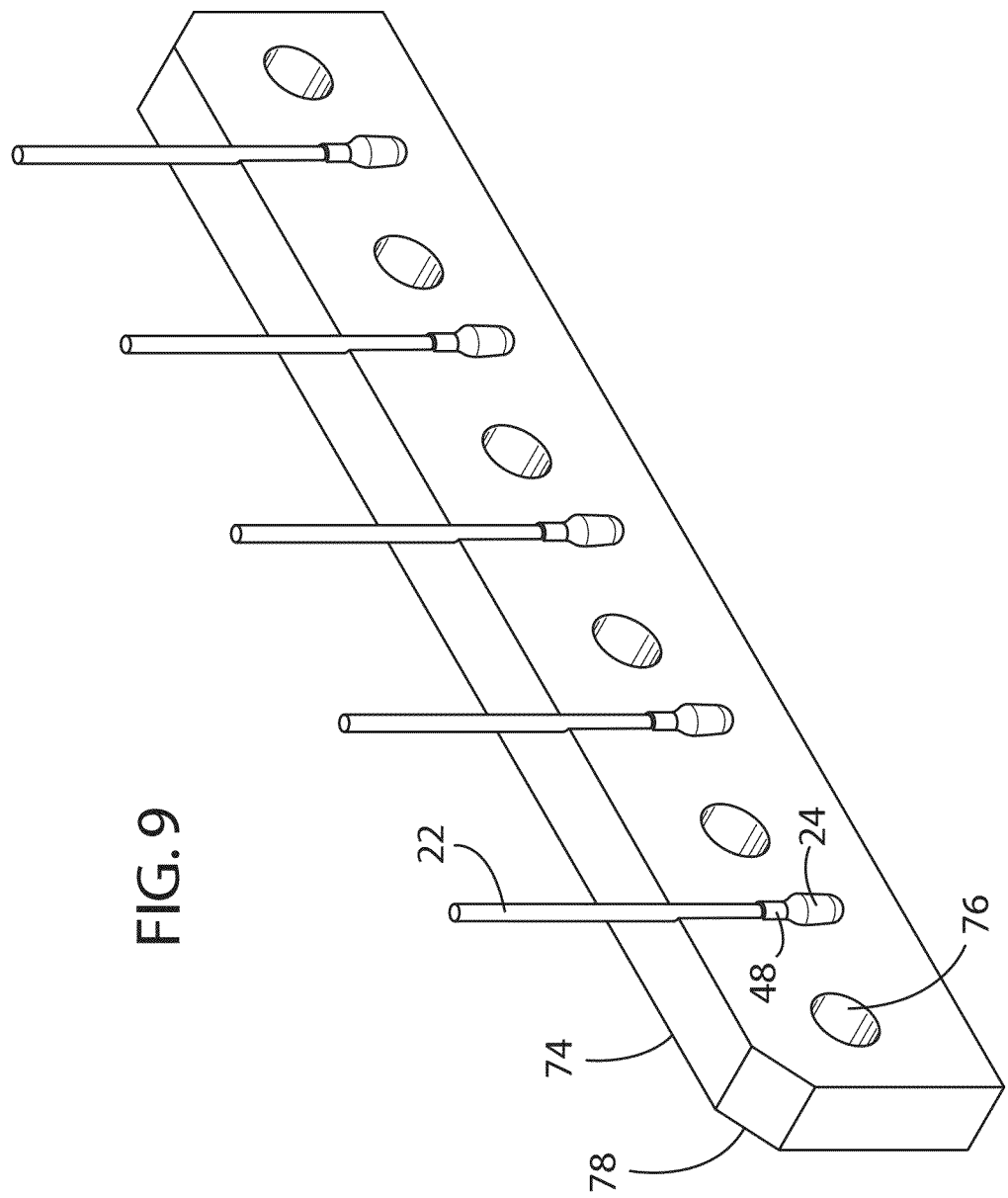
FIG. 9 is a perspective view of a mold for producing a biologic sample collection device as described herein.
Figure 10:
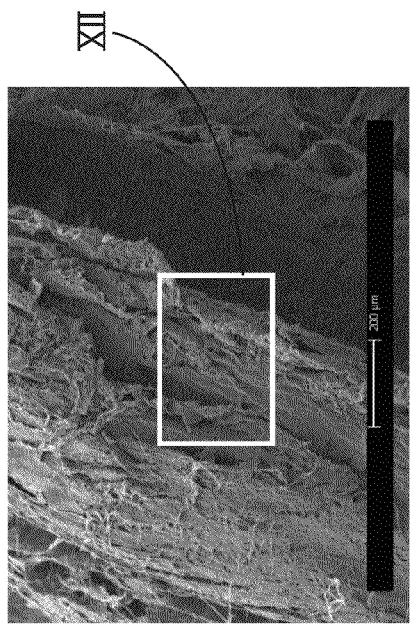
FIG. 10 is a micrograph of a PCL portion of a biologic sample collection device described herein in a biological sample extraction system at 500 µm.
Figure 11:
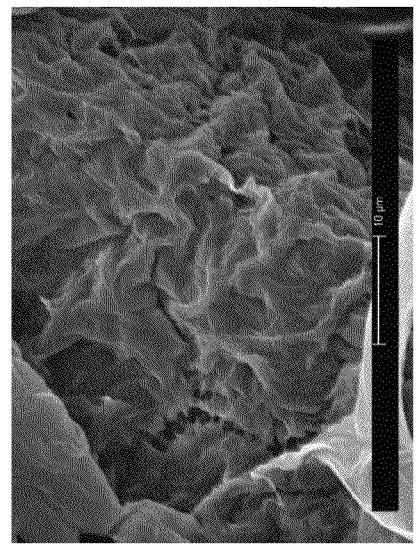
FIG. 11 is a micrograph of the PCL portion shown inset in FIG. 10 at 200 µm.
Figure 12:
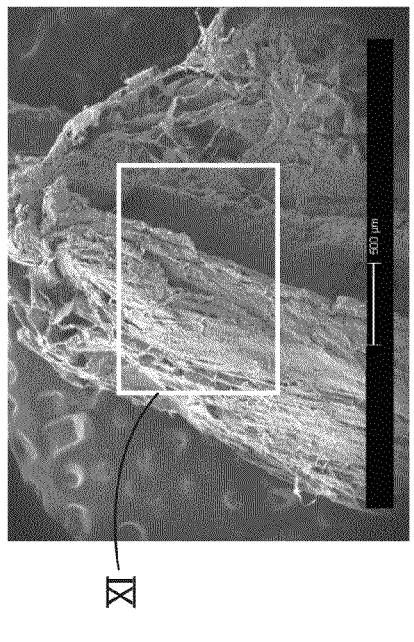
FIG. 12 is a micrograph of the PCL portion shown inset in FIG. 11 at 50 µm.
Figure 13:
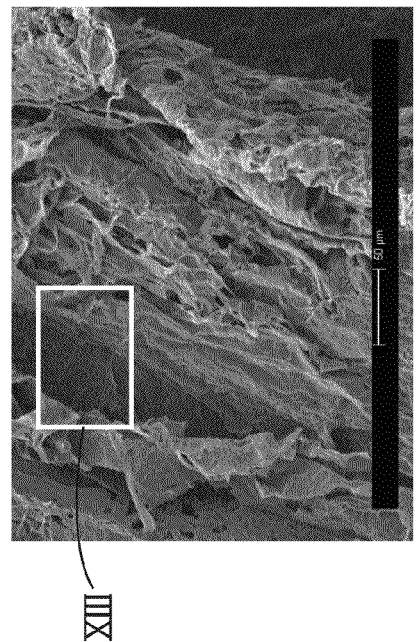
FIG. 13 is a micrograph of the PCL portion shown inset in FIG. 12 at 10 µm.
Figure 23:
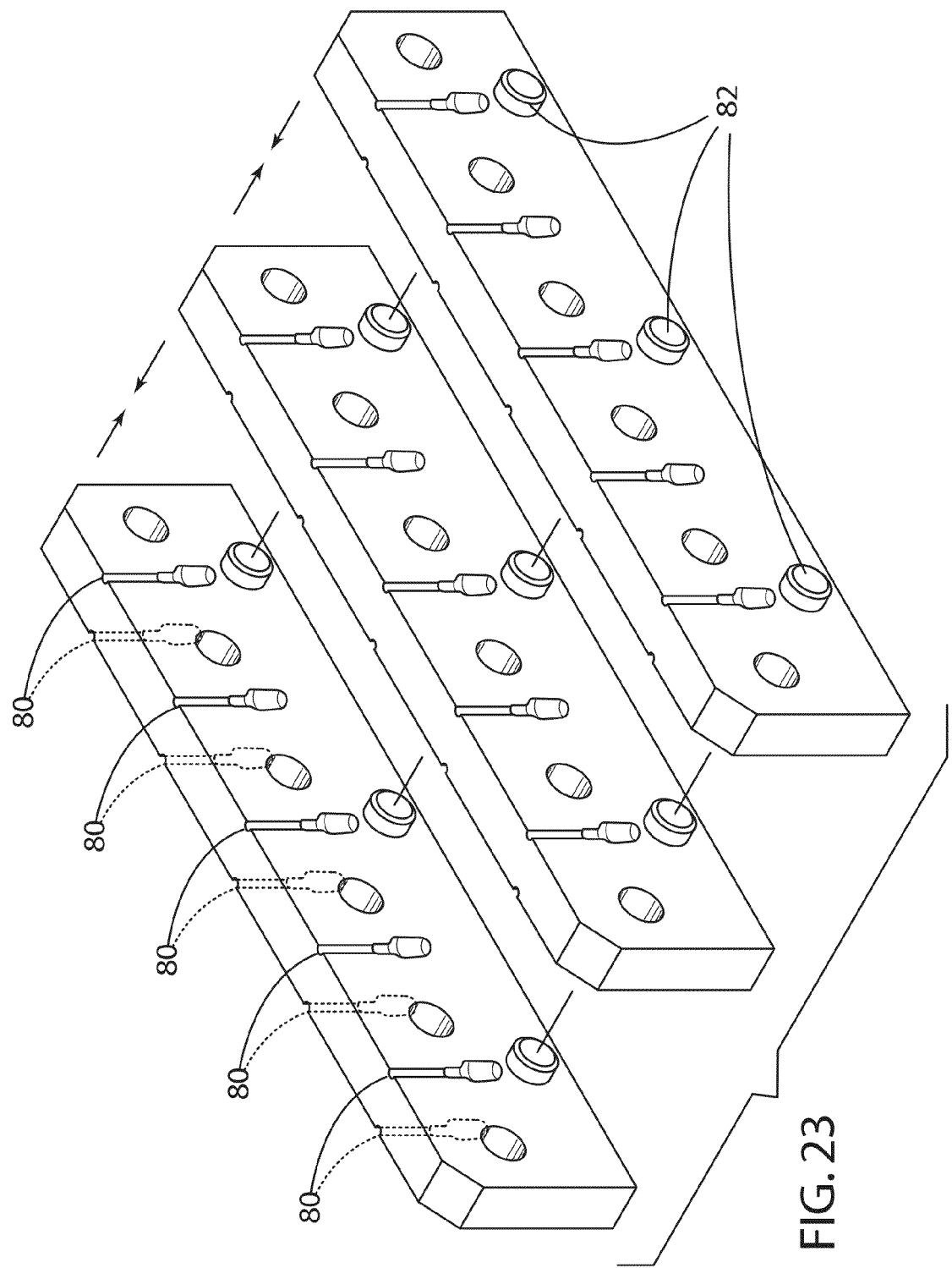
FIG. 23 is an exploded perspective view of another embodiment of a mold for producing a biologic sample collection device as described herein.

Next, at step 56, the PCL solution equilibrated to ambient temperature is delivered to molds having wells that are configured to be in the shape of the desired swab, such as the exemplary swabs shown in FIGS. 4-8 and 15-21. Several forms can be used depending on the final use of the swab or even as a sheet of material (FIG. 21). Exemplary mold configurations are shown in FIGS. 9 and 22-23. Molds can be formed from metals and the like and even coated with a fluoropolymer coating such as on sold under the trade name TEFLON®. Mold materials should be selected to have no or little reaction with the solute. For example aluminum is corrosive in the presence of an acid. As shown, molds 74 can be formed as opposing halves that can be clamped together by a clamping device extending through holes 76 and can provide a plurality of wells 80. As shown in FIG. 23, molds can be clamped together in a series and oriented with precision using pins 82 extending into reciprocal holes (not shown) on the adjacent mold. Here wells 80 are on both sides of the mold half.

Next, at step 58 stems (i.e., carriers) are placed where desired through mold well 80 to allow the solution to envelop the swab and form a swab assembly. Stems may have, at one end, a cap/seal that fit the tube (i.e., a first container) used in step 70 as described above.

Once stabilized (i.e., stems are in place and the solution with matrix material is in the mold well 80), at step 60 the swab assembly is cooled below ambient temperature. In one approach, the assembly is exposed to an environment of about −20° C. (range of about 18-30 degrees Celsius). This step can last from 4 to 24 hours, usually it lasts 6 to 18 hrs. A further cooling step can also optionally be applied to swab. For example, in this additional step the environment is maintained at about −80° C. for about an additional 2-8 hours, most frequently for about 4 to 6 hours. The rate of cooling should be at a rate that will not cause crystallization. Accordingly, any exposure to about −80 degrees Celsius may not provide an acceptable product.

Following the cooling step, the assembly can be removed from the mold at step 62 and submerged in liquid nitrogen to avoid melting if there is any delay before going to step 64. This step maintains the temperature until the lyophilization step below.

Next, at step 64 the swab assembly is freeze dried (lyophilized). This step can last for about 20-24 hours in a chamber of about −50 degrees Celsius (−40 to −60 range). Alternatively the drying step can be done at ambient temperature for 2 to 4 days depending on the solvent used and the shape and size of the swab. Ambient temperature drying may be most viable in sheet embodiments (FIG. 21).

Figure 14:
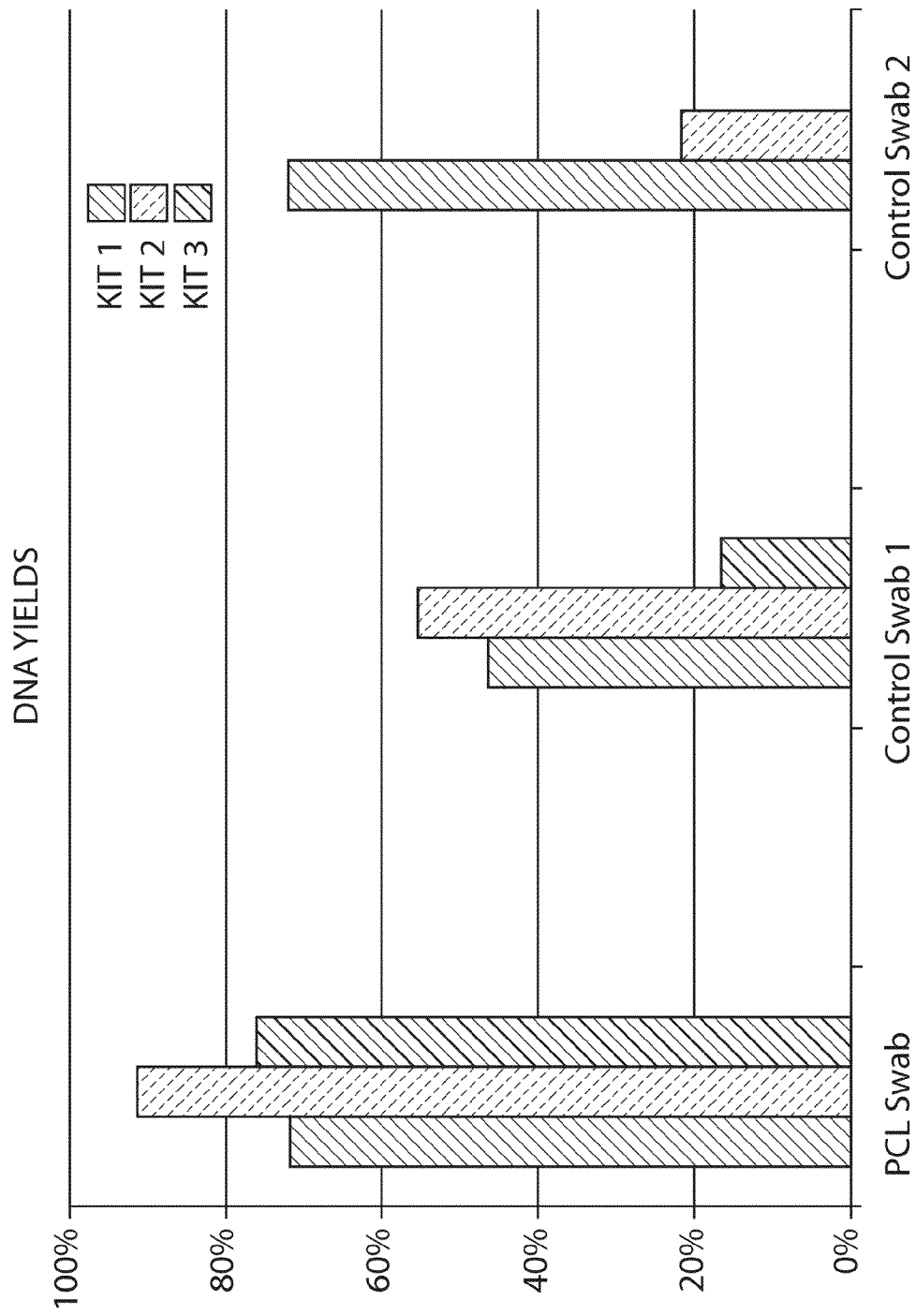
FIG. 14 is a graph comparing DNA yields using a biologic sample collection device as described herein with controls.

Following lyophilization or drying, the assembly can by treated (washed) at step 66 with a strong base solution (e.g., having a pH greater than about 12) and tested for water uptake at step 68. Such treatment can use about 2 N NaOH (sodium hydroxide), and then the swab is neutralized, treated, and dried. This step can increase the swab's ability to take up water (i.e., its hydrophilicity). The NaOH treating step may partially hydrolyze the swab to expose hydroxyl groups. Potassium hydroxide and other types of bases may also work. This treatment step may also improve hydrophilicity with swabs made from other copolymers. Optionally, other types of hydrophilic proteins can be used for the swab matrix that eliminate the need for this step. PCL is still preferably used because it works best with DNA extractions. The yield of DNA is not only good, but it also can allow for better or more amplification. Prior art cotton swabs do not release DNA as well as shown in FIG. 14, which is described below. In one embodiment, referring to step 68 of FIG. 3, swabs are immersed in a beaker with 2 N NaOH and placed on a shaker for 24-48 hours at room temperature. They are then treated until the treatment water has a neutral pH (e.g., a pH of about 7). Usually 5 treatments are sufficient. The swabs as described herein can then be allowed to dry for 18-24 hrs either in an open container or under minimum vaccuum. At predetermined production intervals the resultant swabs can be tested by exposure to 50 µl of water containing 0.2 percent trypan blue. Previous to treatment, the solution forms a bead on the surface of a PCL swab. After successful treatment of the PCL swab as described above, the colored water spreads over the surface of the swab which absorbs a significant fraction of the 50 µl. A further test involves weighing of the swab before and after exposure to 50 µl of water; a weight increase of at least 40 mg (40 µl) indicates that the swab is sufficiently hydrophilic for use.

It is noted that long exposure to NaOH (e.g., more than 3 days) or exposure at elevated temperatures (e.g., greater than about 37 degrees Celsius) will result in dissolution of swab head. Similarly, exposure to strong acids has no effect on the hydrophilic properties of the PCL.

Next, at step 70 the swab assembly is finalized by combining the swab with tubes, sealing caps, packaging, and the like. Assembly is preferably done in a laminar flow hood. Clean rooms and sterile environments can also be beneficial.

Next, at step 72, the swab assembly can be sterilized. In one approach this can be by UV light exposure, though other methods, such as gamma irradiation, are possible so long as the treated swab matrix integrity and desired water uptake is maintained. This step sterilizes and renders the swab DNA free. In one approach, UV exposure can by about 20 minutes with 5000 microjoules/cm$^2$. In another approach, UV radiation can be in two 15 minute cycles of 6000 microjoules/cm$^2$ using exposure indicators in the chamber and in control packages to assure exposure. Biologic samples collected for use in identification of individuals should provide rigorous extraction and amplification to obtain a quantity of DNA of sufficient quality for use in assays to determine allelic forms of multiple pre-selected genes, such as used for developing DNA profiles. Conventional collection swabs have characteristics that render them unusable for the required analyses when paired with certain commonly used commercial DNA extraction kits. In some embodiments, a swab as described herein is soluble in DNA extraction solutions of detergents having, for example, protease K. In other embodiments, the swab is soluble in DNA extraction solutions having a chaopropic agent.

A swab as described herein can be composed entirely from modified (treated) PCL or derivatives or copolymers thereof. For example, in some embodiments, one can use PCL or a PLC derivative material to surface modify a known preformed swab composition. For example, a commercially available polyurethane foam swab used for a variety of purposes (e.g., cleaning, applying paint, make-up etc) can be dipped in PCL to provide the advantages of PCL with special shapes. Such embodiments provide a choice from the large selection of existing swabs and thus selecting those of optimum shapes for given applications. The PCL used in this way can be prepared and applied to the existing swab (substrate) in several ways, which is facilitated by the adherence of PCL to hydrophobic substances.

Although a typical embodiment of a biologic sample collection device includes soluble and hydrophilic PCL coupled to a carrier, in some embodiments, no carrier is required. For example, one could use a piece of soluble, hydrophilic PCL (e.g., obtained from a sheet of soluble and hydrophilic PCL or removed from a biologic sample collection device as described herein and manipulate it with a forceps) for collecting a biologic sample from which nucleic acids can be extracted.

EXAMPLES

The present invention is further illustrated by the following specific examples. The examples are provided for illustration only and should not be construed as limiting the scope of the invention in any way.

Example 1

Treatment and Modifications of PCL

Figure 27:
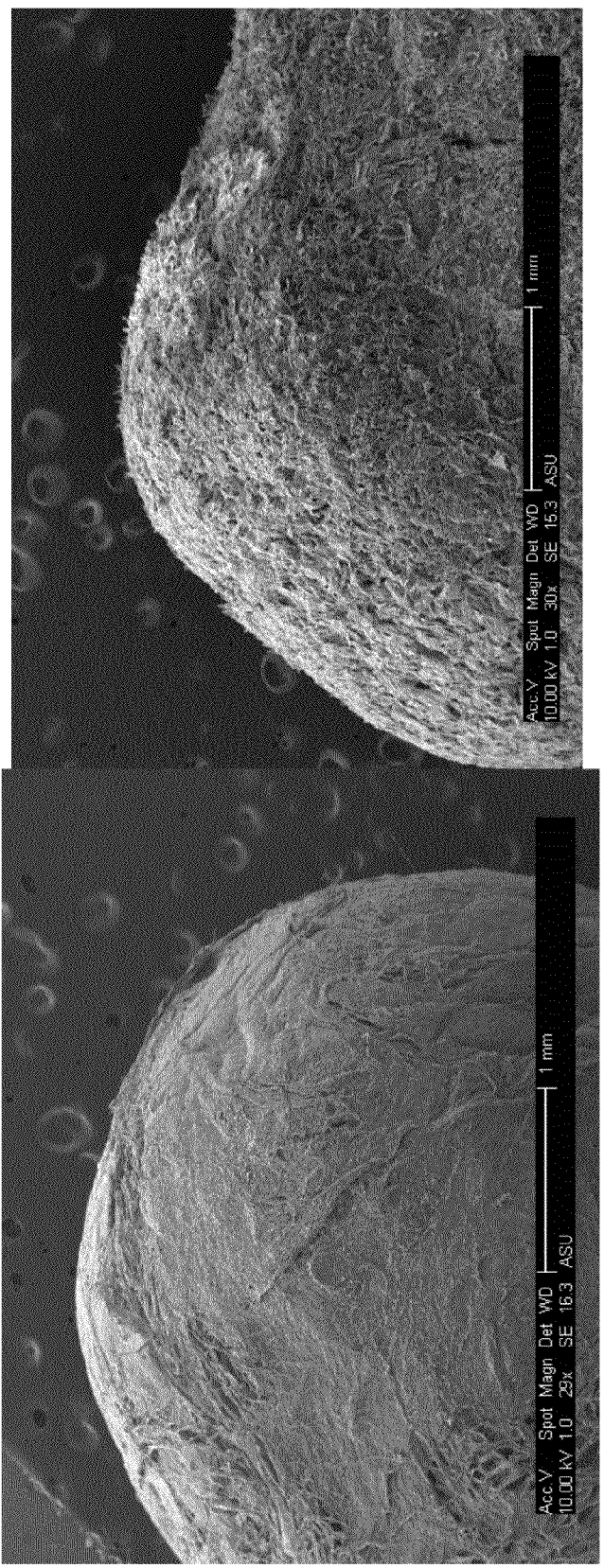
FIG. 27 is a scanning electron micrograph (SEM) of an untreated PCL portion of a biologic sample collection device as described herein (left panel) and of a PCL portion of a biologic sample collection device as described herein that was treated with NaOH (right panel).

FIG. 27 shows scanning electron micrographs of a PCL swab that was treated with NaOH in the following manner.

The swab was treated with 2 N NaOH for 18 hrs at room temperature, neutralized by washing with water until washes were below pH8 and dried. The swab treated in this manner was compared (at the same magnification) to one prior to such treatment. Note that the untreated swab is smoother and lacks the fuzzy surface of the NaOH treated swab.

FIGS. 10-13 show photomicrographs of the surface of a modified PCL swab at 500, 200, 50 and 10 μm. These micrographs show that the treated PCL has a deformed and crumpled appearance having even pores between patches.

The modified PLC swab materials prepared as described herein were tested for DNA yields, the results of which are shown in Table 1 below and FIG. 14.

TABLE 1

| Description | Extraction Kit | Total DNA yield (ng) | Std Dev | Fraction of blood alone (×100 = %) |
|---|---|---|---|---|
| PCL Swab | Kit A | 57.9 | 19.1 | 0.71481481 |
|  | Kit B | 105 | 8.2 | 0.91304348 |
|  | Kit C | 49 | 12 | 0.76323988 |
| Control Swab 1 (cotton) | Kit A | 37.5 | 14.8 | 0.46296296 |
|  | Kit B | 63.8 | 10 | 0.55478261 |
|  | Kit C | 10.6 | 1.4 | 0.16510903 |
| Control Swab 2 (Poly-Nipaam) | Kit A | 58 | 16.5 | 0.71604938 |
|  | Kit B | 25 | 17.7 | 0.2173913 |
|  | Kit C | 0 | 0 | 0 |
| Blood alone | Kit A | 81 | 4.2 | 1 |
|  | Kit B | 115 | 21.2 | 1 |
|  | Kit C | 64.2 | 26.5 | 1 |

As shown, the modified PCL swabs were tested with a variety of commonly used, commercially available DNA extraction and amplification kits (Labeled Kit A, B and C). Comparisons of the three kits with modified PCL swab, standard cotton (control swab 1) and a swab made from various engineered materials (e.g., control swab 2 of Poly-Nipaam) show higher DNA yields from the controls.

It was also observed that under defined conditions, the head of the modified PCL swab dissolves in the DNA extraction reagents and the small amount of solute remaining is removed by an early process step. This DNA-containing solution may then be used to carry out subsequent analytic steps with no or minimal interference from the dissolved swab material. The extracted DNA from the swabs of the present embodiments is biocompatible with PCR and STR typing procedures.

Specifically, as shown in FIG. 14, results for 3 different commonly used DNA extraction kits with a modified PCL swab compared to one made with poly N isopropylacrylamide (Nipaam) and to one made with cotton are shown. While improved performance was seen with the treated PCL swab compared to cotton using Kit A (about 45 versus 65 percent), a much greater improvement was seen with Kit B (about 40 versus 90 percent recovery). In terms of absolute yield the Kit B was best but the results with Kit C showed the greatest improvement for PCL versus cotton (about 17-62% or almost 4 fold increase). This result suggests that pairing swab variations with identified DNA extraction process can yield best results. It was noted that the PCL swab was soluble in the extraction buffers of all kits tested, whereas control swab 2 formed a slurry or was otherwise insoluble.

Example 2

Production of a Modified PCL Preformed Swab

One example of a method to produce a modified PCL preformed swab is provided as follows. Commercially available PCL pellets can be dissolved in an agent, such as glacial acetic acid or dichloromethane, or glacial acetic acid and dichloromethane in combination at concentrations from about 2 percent to about 10 percent weight/volume, preferably about 3.5 percent to about 7 percent weight/volume, and most preferably about 5 percent. It is noted that variation of concentrations produces a coating of different pore size. Preformed swabs can be dipped into the composite solution for 5 to 10 minutes to form a uniform coating. The coated swabs are air dried, for example for up to 24 hours. Alternately, PCL coated swabs can be frozen and freeze-dried in a manner described herein for PCL swabs to give desired texture of the PCL. One can also coat the existing swabs with a solution of PCL mixed with a salt, such as sodium chloride in a solution of about equal parts of PCL and the salt. Next, the dried PCL coated swab can be submerged in an aqueous solution to allow the salt to leach out of the swab. Porosity of the finished swab can be varied by altering volume percentages of sodium chloride in the polymer-solvent slurry. Coating thickness can be controlled by the number and duration of immersions in the dip-coating technique. In this method, the coating can be accomplished by short (e.g., five seconds to one minute) successive dipping (e.g., once, twice, three times, four times, etc.) of the swab into the PCL solution. The dipped substrate can be air dried for about 10 to 15 minutes between dipping cycles to apply more uniformly the PCL to the substrate. The treated swab can then be air dried.

As a further variation, a caprolactone monomer can be copolymerized with other monomers such as lactic acid, PEG, and the like. These co-polymerizations can be used to change the properties and behavior of the material including its porosity and hydrophilicity.

Example 3

Pick-Up and Release of DNA from Human Blood Samples

In Table 2, "pick-up and release" data is shown. Pick-up and release is measured by swabbing a glass slide to which was added 1 ul of human blood, and extracting and quantifying DNA from the swab. Release is measured by dropping the blood sample directly onto the swab, allowing it to dry and quantifying DNA as above. A control for both is adding the blood directly to the extraction tube. The data in Table 2 reveal that PCL swabs were an average of 55% efficient when used to pick up a sample from a glass slide and then release the DNA from that sample in a commercial extraction buffer. This number measures pick-up and release of samples. In order to measure release of DNA from sample, the blood sample was dropped onto the swab directly, allowed to dry and the DNA was then extracted. In this case 68% of the DNA in the sample was obtained. Both of these experiments use the amount of DNA from bloods sample dropped directly into the extraction buffer as 100% value.

TABLE 2

Pick-up and release of DNA from human blood samples:

| Sample | Ng DNA | % control |
|---|---|---|
| Pick-up & release | 12.5 | 55 |
| Release | 15.7 | 68 |
| Control | 23 | 100 |

In Table 3, measurements of pick-up and release from swabs retained for up to 7 days at ambient temperature were obtained. The data listed in this table indicate that swabs may be retained after acquisition of a blood sample for at least 7 days with no significant loss of DNA from the sample when compared to a swab that is used immediately after sample acquisition.

TABLE 3

Aging of Blood Samples on X-swab (a biologic sample collection device as described herein)

| Day | DNA obtained (ng)** | % of control* |
|---|---|---|
| 0 | 12.2 | 55 |
| 3 | 12.9 | 58 |
| 5 | 13.2 | 59 |
| 7 | 11.5 | 52 |

*Control consists of 1 ul of human blood added directly to DNA extraction tube; average yield was 22.2 ng DNA
**Results are average of 4 determinations in which 1 ul dried blood was acquired from a glass slide and X-swab extracted using Qiagen reagents on the day after sample collection indicated.

Example 4

Production of Swabs or Swab Materials Using NaOH or $NaHCO_3$

In one example of a method of producing a biologic sample collection device as described herein, the method involves use of NaOH. One embodiment of such a method includes the following steps: dissolving PCL in a PCL dissolving agent at a concentration in the range of about 2 percent to about 10 percent weight/volume, resulting in a PCL composite solution; submersing a carrier at least once into the PCL composite solution such that the PCL composite solution coats the carrier; drying the PCL composite solution-coated carrier; submersing the PCL composite solution-coated carrier in an aqueous solution, whereby the dissolving agent is leached from the PCL composite, resulting in a PCL-coupled carrier; contacting the PCL with a base having a pH greater than 8 (NaOH); washing the PCL with water, or acidic solution, until the PCL has a neutral pH; drying the PCL; and sterilizing the PCL-coupled carrier and rendering it free of nucleic acids, resulting in a biologic sample collection device comprising soluble and hydrophilic PCL coupled to the carrier, wherein the PCL solubilizes when exposed to a nucleic acid extraction reagent.

In another example of a method of producing a biologic sample collection device as described herein, the method involves use of $NaHCO_3$. One embodiment of such a method includes the following steps: dissolving PCL in a PCL dissolving agent at a concentration in the range of about 2 percent to about 10 percent weight/volume, resulting in a PCL composite solution; submersing a carrier at least once into the PCL composite solution such that the PCL composite solution coats the carrier; submersing the PCL composite solution-coated carrier in an aqueous solution having a pH greater than 8 ($NaHCO_3$), whereby the dissolving agent is leached from the PCL composite, resulting in a PCL-coupled carrier; washing the PCL with water, or acidic solution, until the PCL has a neutral pH; drying the PCL; and sterilizing the PCL-coupled carrier and rendering it free of nucleic acids, resulting in a biologic sample collection device comprising soluble and hydrophilic PCL coupled to the carrier, wherein the PCL solubilizes when exposed to a nucleic acid extraction reagent.

Other Embodiments

Any improvement may be made in part or all of the devices, kits and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A biologic sample collection device consisting of: soluble and hydrophilic polycaprolactone coupled to a carrier, wherein the polycaprolactone is optionally coupled to one or more of a carbohydrate trehalose derivative group and at least one protein, and the carrier optionally comprises one or more of an identifying label, a radio-frequency identification tag and a bar code, and wherein at least a portion of the polycaprolactone solubilizes when exposed to a nucleic acid extraction reagent.

2. The biologic sample collection device of claim 1, wherein the polycaprolactone is copolymerized with at least one agent selected from the group consisting of: an acrylamide and a polyester other than polycaprolactone.

3. The biologic sample collection device of claim 2, wherein the at least one agent is selected from the group consisting of: polylactide, polyglycolide, polydioxanone, acrylamide, poly N-isopropylacrylamide, and polyurethane.

4. The biologic sample collection device of claim 1, wherein the biologic sample collection device has been sterilized.

5. The biologic sample collection device of claim 1, wherein the polycaprolactone has been treated with a base having a pH greater than 8 and a neutralizing agent for increasing hydrophilicity.

6. The biologic sample collection device of claim 5, wherein the base is selected from the group consisting of: NaOH, $NaHCO_3$, KOH, $Na_2CO_3$, and $CA(OH)_2$.

7. The biologic sample collection device of claim 1, wherein the at least one protein is selected from the group consisting of: antibody, silk, collagen, fibrin and elastin.

8. The biologic sample collection device of claim 1, wherein the carrier comprises a material selected from the group consisting of: metal, plastic, polymer, wood, and glass.

9. The biologic sample collection device of claim 1, wherein the biologic sample is a human buccal sample.

10. The biologic sample collection device of claim 1, wherein the polycaprolactone is contained within at least one aperture disposed in the carrier.

11. The biologic sample collection device of claim 10, wherein the polycaprolactone is contained within two or more apertures disposed in the carrier.

12. The biologic sample collection device of claim 10, wherein the at least one aperture is disposed at a first end of the carrier, and an identifying label is disposed at a second end of the carrier.

13. A kit comprising:
a) at least one biologic sample collection device consisting of: soluble and hydrophilic polycaprolactone coupled to a carrier, wherein the polycaprolactone is optionally coupled to one or more of a carbohydrate trehalose derivative group and at least one protein, and the carrier optionally comprises one or more of an identifying label, a radio-frequency identification tag and a bar code, and wherein at least a portion of the polycaprolactone solubilizes when exposed to a nucleic acid extraction reagent; and
b) packaging.

14. The kit of claim 13, further comprising instructions for use and at least one selected from the group consisting of: a nucleic acid extraction reagent; a nucleic acid labeling reagent; and a set of reagents for nucleic acid amplification.

15. The kit of claim 13, wherein the packaging comprises a polymer laminate or plastic container.

16. The kit of claim 13, wherein the kit comprises a plurality of biologic sample collection devices.

17. The kit of claim 16, wherein each biologic sample collection device of the plurality of biologic sample collection devices is individually packaged.

18. The kit of claim 13, wherein the packaging comprises: a first container comprising a rigid housing and a cap to which the biologic sample collection device is attached, the biologic sample collection device positioned in the interior of the housing such that when the cap is operably attached to the housing, the biological sample collection device does not contact the interior of the housing; and a second container in which the first container and the biologic sample collection device are contained.

19. The kit of claim 18, wherein the first container is plastic and the second container is a plastic bag.

20. The kit of claim 13, wherein the polycaprolactone is contained within at least one aperture disposed in the carrier.

21. The kit of claim 20, wherein the polycaprolactone is contained within two or more apertures disposed in the carrier.

22. The kit of claim 20, wherein the at least one aperture is disposed at a first end of the carrier, and an identifying label is disposed at a second end of the carrier.

23. The kit of claim 13, wherein the polycaprolactone is copolymerized with at least one agent selected from the group consisting of: an acrylamide and a polyester other than polycaprolactone.

24. The kit of claim 23, wherein the at least one agent is selected from the group consisting of: polylactide, polyglycolide, polydioxanone, acrylamide, poly N-isopropylacrylamide, and polyurethane.

25. The kit of claim 13, wherein the biologic sample collection device has been sterilized.

26. The kit of claim 25, wherein the polycaprolactone has been treated with a base having a pH greater than 8 and a neutralizing agent for increasing hydrophilicity of the polycaprolactone.

27. The kit of claim 26, wherein the base is selected from the group consisting of: NaOH, $NaHCO_3$, KOH, $Na_2CO_3$, and $CA(OH)_2$.

28. A method of producing the biologic sample collection device of claim 1, the method comprising the steps of:
providing a solution of solubilized polycaprolactone;
submersing a carrier at least once into the solubilized polycaprolactone solution such that the solubilized polycaprolactone solution coats the carrier;
subjecting the solubilized polycaprolactone solution-coated carrier to treatment with a base having a pH greater than 8 and a neutralizing agent under conditions that result in soluble and hydrophilic polycaprolactone coupled to the carrier; and sterilizing the soluble and hydrophilic polycaprolactone-coupled carrier such that the soluble and hydrophilic polycaprolactone-coupled carrier is free of nucleic acids, resulting in the biologic sample collection device of claim 1 comprising soluble and hydrophilic polycaprolactone coupled to the carrier, wherein at least a portion of the polycaprolactone solubilizes when exposed to a nucleic acid extraction reagent.

29. The method of claim 28, wherein the carrier is submersed into the solution of solubilized polycaprolactone using a fabricated mold.

30. The method of claim 28, wherein the base is selected from the group consisting of: NaOH, $NaHCO_3$, KOH, $Na_2CO_3$, and $CA(OH)_2$.

31. The method of claim 28, wherein sterilizing the soluble and hydrophilic polycaprolactone-coupled carrier and rendering it free of nucleic acids comprises exposing the soluble and hydrophilic polycaprolactone-coupled carrier to UV radiation.

32. The method of claim 28, further comprising copolymerizing the polycaprolactone with at least one agent selected from the group consisting of: an acrylamide and a polyester other than polycaprolactone.

33. The method of claim 28, further comprising adhering to or coupling to the carrier at least one selected from the group consisting of: a radio-frequency identification tag, a bar code, and an identification label.

34. A method of extracting nucleic acids from a biologic sample collected by the biologic sample collection device of claim 1, the method comprising the steps of:
    contacting the biologic sample and the biologic sample collection device with at least one nucleic acid extraction solution under conditions such that the polycaprolactone is solubilized or dissolved, resulting in a solution comprising nucleic acids separated from the biologic sample collection device; and
    extracting the nucleic acids from the solution.

35. The method of claim 34, wherein the step of contacting the biologic sample and the biologic sample collection device with at least one nucleic acid extraction solution comprises immersing the biologic sample and the polycaprolactone in the at least one nucleic acid extraction solution.

36. The method of claim 34, wherein the at least one nucleic acid extraction solution comprises a proteolytic enzyme.

37. The method of claim 34, wherein the biologic sample is a human buccal sample.

38. The method of claim 34, wherein about 50% to about 95% of the nucleic acids from the biological sample are extracted from the biological sample.

39. The method of claim 34, wherein the carrier comprises a radio-frequency identification tag and the method further comprises obtaining information from the radio-frequency identification tag, wherein the information is at least one selected from the group consisting of: date, time, person, location, collector, and case number.

40. A method for collecting a biologic sample, the method comprising the steps of:
    contacting the biologic sample collection device of claim 1 with a biologic sample such that the biologic sample is reversibly adhered to the polycaprolactone;
    contacting the biologic sample collection device and the biologic sample with at least one nucleic acid extraction reagent under conditions such that the polycaprolactone is solubilized and the sample is separated from the biologic sample collection device; and
    collecting the separated sample.

41. The method of claim 40, further comprising extracting nucleic acids from the separated sample.

42. The method of claim 41, wherein the nucleic acids consist of deoxyribonucleic acid.

43. A method of producing the biologic sample collection device of claim 1, the method comprising the steps of:
    providing a solution of solubilized polycaprolactone;
    forming at least a first flat sheet of solubilized polycaprolactone;
    subjecting the at least first flat sheet of solubilized polycaprolactone to treatment with a base having a pH greater than 8 and a neutralizing agent under conditions that result in soluble and hydrophilic polycaprolactone that solubilizes when exposed to a nucleic acid extraction reagent;
    coupling the at least first sheet of soluble and hydrophilic polycaprolactone to a carrier; and
    sterilizing the soluble and hydrophilic polycaprolactone-coupled carrier such that the soluble and hydrophilic polycaprolactone-coupled carrier is free of nucleic acids, resulting in a biologic sample collection device comprising soluble and hydrophilic polycaprolactone coupled to the carrier, wherein the soluble and hydrophilic polycaprolactone is a flat sheet, and at least a portion of the soluble and hydrophilic polycaprolactone solubilizes when exposed to a nucleic acid extraction reagent.

* * * * *